(12) United States Patent
Jiang et al.

(10) Patent No.: US 12,040,049 B2
(45) Date of Patent: Jul. 16, 2024

(54) DIRECTIONAL POLYMERISATION FLUORESCENT PROBE PCR AND TEST KIT

(71) Applicant: Hong Jiang, Zhuhai (CN)

(72) Inventors: Hong Jiang, Zhuhai (CN); Yue Qu, Zhuhai (CN); Chaoqi Qu, Zhuhai (CN)

(73) Assignee: Hong Jiang, Zhuhai (CN)

( * ) Notice: Subject to any disclaimer, the term of this patent is extended or adjusted under 35 U.S.C. 154(b) by 368 days.

(21) Appl. No.: 17/059,479

(22) PCT Filed: Jul. 2, 2019

(86) PCT No.: PCT/CN2019/094327
§ 371 (c)(1),
(2) Date: Nov. 30, 2020

(87) PCT Pub. No.: WO2019/228541
PCT Pub. Date: Dec. 5, 2019

(65) Prior Publication Data
US 2021/0207204 A1    Jul. 8, 2021

(30) Foreign Application Priority Data
May 31, 2018  (CN) .......................... 201810550792.8

(51) Int. Cl.
*C12Q 1/68*      (2018.01)
*C12Q 1/6848*    (2018.01)
(Continued)

(52) U.S. Cl.
CPC ............ *G16B 25/20* (2019.02); *C12Q 1/6848* (2013.01); *C12Q 1/686* (2013.01); *C12Q 1/6876* (2013.01); *G16B 25/00* (2019.02)

(58) Field of Classification Search
CPC ....................................................... C12Q 1/68
(Continued)

(56) References Cited

U.S. PATENT DOCUMENTS

2016/0237472 A1 * 8/2016 Jiang ................ C12Q 1/6848

FOREIGN PATENT DOCUMENTS

| CN | 103114131 A | * | 5/2013 | ........... C12Q 1/6848 |
| CN | 103205425 A | * | 7/2013 | |
| CN | 108085372 A | * | 5/2018 | ........... C12Q 1/6848 |

* cited by examiner

*Primary Examiner* — Aaron A Priest
(74) *Attorney, Agent, or Firm* — Bayramoglu Law Offices LLC

(57) ABSTRACT

A directional polymerisation fluorescent probe PCR and a test kit, wherein directional primer pair 5' end complementary binding, sensitising, fluorescent probe 3' end directional polymerisation and melting PCR are performed on the basis of primers and probe specific sequences, primer design uses pair side original primer 5' end 5-10 bp reverse base sequences, added to primer pair front ends according to the 5'-3' direction to form a "5' reverse complementary sequence" chimeric primer pair for directional polymerisation, and 5' complementarity enables amplification product 3' ends to also be mutual templates and mutual primers for amplification. Sensitivity is increased by >2$^n$ geometric progression amplification, and competition decreases primer 3' polymerisation PD non-specificity. Conventional hydrolysis fluorescent probe 3' ends are added to probe central portion reverse complementary 5-8 bp end sequences to form two probe molecules for end portion-central portion close mutual hybridisation and directional polymerisation. Fluorescein-quenching groups at both ends of the probes are close to reduce reaction baseline fluorescence, and probe self-polymerisation inhibits primer polymerisation non-specificity. Once long sequence target molecule chains compete for hybrid primers and probe chains, polymerisation primer pairs and probes with weak relative binding forces melt and bind to target template molecules for amplification, (Continued)

and probes are hydrolysed by polymerase to produce fluorescence.

10 Claims, 4 Drawing Sheets

Specification includes a Sequence Listing.

(51) Int. Cl.
      *C12Q 1/686*       (2018.01)
      *C12Q 1/6876*     (2018.01)
      *G16B 25/00*      (2019.01)
      *G16B 25/20*      (2019.01)

(58) Field of Classification Search
      USPC ....................................................... 435/6.12
      See application file for complete search history.

```
                         SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 1 aatgcccta tcttatcaac                                                  20

<210> SEQ ID NO 2
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 2
agattgagat cttatgcgac                                                 20

<210> SEQ ID NO 3
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 3
tcaatctccg gaaatgcccc tatcttatca a                                    31

<210> SEQ ID NO 4
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 4
ggcatttccg gagattgaga tcttatgcga c                                    31

<210> SEQ ID NO 5
<211> LENGTH: 31
<212> TYPE: DNA
<213> ORGANISM: Artificial Sequence
<220> FEATURE:
```

```
<223> OTHER INFORMATION: The sequence is synthetized.

<400> SEQUENCE: 5
cgtctgcgag gcgagggagt tcttcttcta a                              31

<210> SEQ ID NO 6
<211> LENGTH: 35
<212> TYPE: DNA
<213> ORGANISM: Artificial Sequence
<220> FEATURE:
<223> OTHER INFORMATION: The sequence is synthetized.

<400> SEQUENCE: 6
cgtctgcgag gcgagggagt tcttcttctc cctca                          35

<210> SEQ ID NO 7
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 7
caaatgcccc tatcttatca                                           20

<210> SEQ ID NO 8
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 8
gtcgcagaag atctcaatct c                                         21

<210> SEQ ID NO 9
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 9
atgggcatct tataaggtga a                                         21

<210> SEQ ID NO 10
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 10
gaggatctta taggtgagcc a                                         21

<210> SEQ ID NO 11
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 11
gatcctccgg atgggcatct tataaggtga a                              31
```

```
<210> SEQ ID NO 12
<211> LENGTH: 30
<212> TYPE: DNA
<213> ORGANISM: Artificial Sequence
<220> FEATURE:
<223> OTHER INFORMATION: The sequence is synthetized.

<400> SEQUENCE: 12
gcccatccgg aggatcttat aggtgagcca                                        30

<210> SEQ ID NO 13
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 13
ctcatggcaa gaaagtgctc ggtgcctttta a                                     31

<210> SEQ ID NO 14
<211> LENGTH: 27
<212> TYPE: DNA
<213> ORGANISM: Artificial Sequence
<220> FEATURE:
<223> OTHER INFORMATION: The sequence is synthetized.

<400> SEQUENCE: 14
agcgatccgg taggcgaacc ctgccca                                           27

<210> SEQ ID NO 15
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 15
cgcctaccgg atcgctgatc cggccaca                                          28

<210> SEQ ID NO 16
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 16
cacataggtg aggtctgcta cccacagccg acctca                                 36
```

DIRECTIONAL POLYMERISATION FLUORESCENT PROBE PCR AND TEST KIT

CROSS REFERENCE TO THE RELATED APPLICATIONS

This application is the national phase entry of International Application No. PCT/CN2019/094327, filed on Jul. 2, 2019, which is based upon and claims priority to Chinese Patent Application No. 201810550792.8, filed on May 31, 2018, the entire contents of which are incorporated herein by reference.

TECHNICAL FIELD

This invention belongs to the molecular biology nucleic acid detection technology field, especially relates to a fluorescent probe PCR technology of the 5' ends of directed primer pair complementary binding and sensitizing, and the 3' ends of hydrolysis probes polymerizing and melting.

BACKGROUND

Nucleic acid amplification PCR technology was developed and matured with the progress of modern molecular biology. As early as 1953, the nucleic acid DNA double helix model and semi-reserved replication started the modern molecular biology era and laid the foundation of Polymerase Chain Reaction (PCR). Even Khorana directly proposed the mode of nucleic acid in vitro amplification in 1971: "After DNA denaturation, hybridize with appropriate primers, extend the primers with DNA polymerase, and repeat the process, then the tRNA gene can be cloned". In 1985, Kary Mullis of the Human Genetics Laboratory of PE-Cetus company, USA, got the inspiration for nucleic acid amplification when studying one-way nucleic acid sequencing: simulate the exponential replication of natural DNA bi-directed amplification in a test tube. Provide a suitable condition-template DNA, oligonucleotide primers, DNA polymerase, suitable buffer system, temperature and time for DNA denaturation, renaturation and extension, then a piece of DNA molecule with known sequences at both ends can be amplified exponentially. After a series of exploration, development, and invention and application of thermostable polymerase and thermal cycler, Cetus company applied for the first PCR invention patent in 1987 (U.S. Pat. No. 4,683,202).

PCR technology has become the core basic technology of life science research due to its unique characteristics of high sensitivity, strong specificity, simplicity and speed, and low purity requirements. However, traditional PCR (also known as terminal PCR) requires product gel electrophoresis detection to analyze the results. Traditional PCR can only detect the qualitative nature of the final product of the reaction but cannot accurately quantify it due to the limitation of large variation in the amount of PCR product. At the same time, it does not solve the problems of aerosol pollution, primer dimers, non-specific amplification, etc. Therefore, the traditional PCR combining with product gel electrophoresis detection or blot method is not suitable for clinical examination and other applications. In 1992, Higuchi et al. first proposed using dynamic PCR method and closed fluorescence detection method to analyze the number of target genes, and put forward new ideas for solving the problems of traditional PCR. In 1996, the American company Applied Biosystems introduced the real-time fluorescent quantitative PCR technology. The so-called real-time fluorescent quantitative PCR technology (BioTechniques 1997, 22: 130-138), means the real-time fluorescent PCR quantitative analysis is to quantify by correlating real-time detection of the amount of amplified product (product labeling fluorescent intensity) directly to the amount of initial target gene. The cycle number Ct value (Cycle threshold) at which the increased fluorescence signal of the amplified product reaches the logarithmic phase has a negative linear relationship with the logarithm of the initial copy number of the target template. That is, the amplification cycles required to achieve the same fluorescence intensity of log phase for double dilution of starting template is increased by one cycle number (Ct). This technology implements a completely closed-tube operation, avoids the product contamination problem caused by traditional PCR open lid, reduces the occurrence of false positive results, and also avoids environmental pollution. Compared with the traditional PCR electrophoresis method, this technology is easy to operate, and the detection results are displayed in more intuitive curve data, so as to determine the positive, negative and suspicious results of samples, ensure the accuracy of the results.

The increased signal of the real-time fluorescent quantitative PCR amplification product can be displayed by the dye method or detected by the method of fluorescent probe with quenching group. The dye method is to add an appropriate amount of fluorescent dye (such as SYBR Green I) to the PCR reaction system. After the fluorescent dye is non-specifically incorporated into the DNA double-strand, it emits a fluorescent signal. The dye molecule that is not incorporated into the strand will not emit any fluorescent signal, thus ensuring that the increase of fluorescence signal is completely synchronized with the increase of PCR product. The non-specific dye method has low cost, but faces the problem of false positives similar to the interference of non-specific amplification products of traditional PCR. The probe method means when a pair of primers are added during PCR amplification, a specific fluorescent probe is added at the same time. The probe is an oligonucleotide, and both ends are labeled with a reporter fluorescent group and a quenching fluorescent group separately. When the probe is complete, the fluorescent signal emitted by the reporter group is absorbed by the quenching group. During PCR amplification, the 5'-3' exonuclease activity of Taq enzyme digests and hydrolyzes the probe to separate the reporter fluorescent group from the quenching fluorescent group, so that the fluorescence monitoring system can receive the fluorescent signal. That is, every time a DNA strand is amplified, a fluorescent molecule is formed, so that the accumulation of fluorescent signal is completely synchronized with the formation of PCR products. Compared with the dye method, the probe method avoids the occurrence of false positive problem to a certain extent. Its specificity is guaranteed by both primers and probes, which further increases the credibility of the results.

The quenched fluorescent probe can be activated by degradation. For example, in 1995, PE company of US developed a fluorescence labeled probe hydrolyzed by Taq enzyme and real-time fluorescent quantitative PCR technology (Livak K J, et al., 1995, Genome Res: 4:357-362), and applied for a patent for the invention of hydrolysis probe (trade name: TaqMan) PCR in 1997 (U.S. Pat. No. 6,485,903); and Epoch company's MGB probe with minor groove binder group on the basis of hydrolysis fluorescent probes (U.S. Pat. No. 7,205,105). Compared with the TaqMan probe, this probe improves the interference of the background signal. Its shorter probe design not only enhances the quenching effect, reduces the fluorescence background, but also can better distinguish alleles and can detect single nucleotide polymorphism (SNP). In 2009, Igor V. Kutyavin in the United States proposed a new PCR detection technology-Snake system (Nucleic Acids Res. 2010, 38(5)e29). This system by adding a specific base fragment that has the same sequence as the front sequence of 5' end binding site of the primer amplification product probe at the 5' end of a primer, makes the self 3' end of the product amplified again can form a stem-loop secondary structure, then extend and hydrolyze probe to be the best substrate for Taq enzyme 5'-3' exonuclease activity, which enhances the fluorescence intensity of the amplified product. Unlike TaqMan, the Snake system can use shorter probes to improve the fluorescence background, and has strong advantages in signal generation and sequence detection, especially in single nucleotide detection.

Quenched fluorescent probes can also be activated by secondary structure changes. Molecular beacon (Tyagi S, et al, 1996, Nat Biotechnol 14:303-308) is such a hybrid probe with stem-loop or panhandle structure, and it was filed a Molecular beacon invention patent in 1999 (U.S. Pat. No. 05,925,517). This structure makes the fluorescent group and the quenching group closely contact, thereby effectively solving the high background fluorescence problem of TaqMan, but the product signal is too weak due to incomplete quenching removal. Other dual hybridization (FRET) probes, scorpion probes, Sunrise-Primer, Lux Pimers, etc., the scope of their use is limited to certain applications, they are not significantly better than the hydrolysis probe TaqMan method, and the route and principle is different from TaqMan and MGB probes. At present, the most widely used clinical test is the hydrolysis probe TaqMan Real-time PCR.

However, the sensitivity of Real-time PCR is still slightly insufficient. With one more signal conversion in the probe method Real-time PCR, each product produces at most one fluorescent group, so the sensitivity is lower. The detection of femtogram fg/ml level or single-digit target molecule copy requires amplifying to 38 cycles, and then a nested PCR with outer and inner primers of two-step amplification appeared (J Med Virol, 30-2:85). It uses outer primers to pre-amplify for 15-30 cycles to improve sensitivity, and add inner primers to continue amplifying for 25-30 cycles, and tt even provides the possibility to detect a single target molecule with extremely high sensitivity of exponential amplification of more than 40 cycles. And with the addition of the new reaction components of the nested PCR, the time from the exponential form or logarithmic phase to the so-called "stagnation effect" plateau is also delayed, and the geometric amplification efficiency of 2n series is maintained. However, the outer primers of nested PCR increase the complexity of the system and increase the non-specificity of two rounds of PCR. The residue of the outer primer promotes the non-specific amplification of the inner primer, and increases the non-specificity of CT value 30 cycles of the general conventional primer background to the non-specificity of background before Ct value <25 cycles. The increased non-specificity of the nested or two rounds of PCR counteracts the amplification effect of the first round or outer primers' pre-amplification. Pre-amplification needs to take out at least 20-50 times dilution or purify the target product by gel electrophoresis to remove the influence of outer primers to eliminate the increase of non-specificity of the system, which not only increases the complexity of the operation, but also brings product aerosol cross-contamination risk caused by PCR post-processing.

Conventional PCR detecting the final reaction-plateau amplification products, generally only needs 25 to 30 cycles of amplification. But the Real-time PCR detects the Ct value of the cycle number at the initial logarithmic stage, and PCR quantification with labeled probes such as TaqMan requires 40 cycles of amplification; and Real-time PCR based on the fluorescent dye SYBR Green I sometimes needs to increase to 45 cycles in order to detect non-specific background. In a general PCR reaction system, there are not only specific amplification of primers binding to target templates, but also excess primers and excess non-specific templates, including non-specific amplification of polymer from hybridization and extension of primers and primers, or primer and probe or other short Oligo. But the non-specificity of only one primer is far behind the exponential non-specificity, and only 3' end complementary extension of a pair of excessive primer can produce exponential non-specific amplification. Primer dimers are generally formed by dint of pairing of multiple complementary bases at the 3' end, being primer to each other to extend. Continuous reverse complementary sequences between primer pairs can be avoided by conventional primer design method, but 1-2 base complementation at the end is inevitable. Since the single strand of DNA can be bent and turned, the 1-2 complementary bases at the 3' end of the primer pair are not enough to independently form a stable hydrogen bond, but they can still be combined by the hydrogen bonding force of multiple complementary bases including multiple discontinuous complementary bases outside the the 3' end after the primer is turned. Extend a few bases to produce a stable complementary sequence then produce a complete primer dimer, and the dimer is used as a template to bind primers to form a large number of non-specific amplifications and binds dyes in the subsequent thermal cycle. In SYBR Green I dye-based real-time PCR experiments without template, the cycle threshold (Ct value) for most primer pairs to produce dimer is generally about 30 cycles (Jannine Brownie, et al, 1997, Nucleic Acids Research 25: 3235-3241), which severely interferes with the quantification or misreading of low-concentration target molecule. What is also overlooked is that real-time PCR with probes such as TaqMan also has the problem of primer dimers. Although the primer dimer does not directly interfere with the TaqMan probe binding, the primer dimer does not emit fluorescence, but it competitively consumes PCR reagent components including primers, polymerase, enzyme substrates, etc., significantly competitively inhibits specific amplifying efficiency of low-concentration target, and further reduces the detection sensitivity of TaqMan probe real-time PCR.

In real-time PCR reactions with probes such as TaqMan, a pair of excessive primers will also hybridize and polymerize with excessive longer probes. Firstly, two incomplete dimers of primers and probes sequences hybridized and partially extended are generated, then the two incomplete dimers are used as primers for each other in the PCR thermal cycling reaction to hybridize, extend and be exponentially amplified non-specifically and largely, and "primer-partial probe-primer" polymers with partial probe sequence are generated. Generally, the labeling rate of both ends of the probe sequence is only about 70%-80%; and the remaining 20% of the probe Oligo with free 3' end hydroxyl will directly hybridize with the 3' ends of the two kinds of primers, extend and be amplified exponentially, which brings non-specific amplification of "primer-probe" polymerization and false positive reactions (Qianfeng Xia. Development and clinical application of dimer mutation primers quantitative PCR technology [D]. Chongqing Medical University, 2011.). Without template, any pair of primers and TaqMan probe background fluorescence PCR produces a non-specific amplification curve with a Ct value of 33-35 cycles. And as the same PCR amplification is repeated repeatedly, the fluorescence absorption peak of the amplification plateau becomes higher and higher, and the background Ct value gradually moves forward, resulting in certain sample detection false positives. The dimers and trimers of part of the probes sequences will compete with the specific target molecules for the probes, and on the contrary, it will weaken the hydrolysis of the labeled fluorescent group at the 5' end, and decrease the detection sensitivity of the system or fail to detect weak positive samples, also multiple polymerization amplification increases the complexity of the system.

TaqMan—the innovation of molecular beacon, solves the problem of baseline fluorescence to a certain extent, but the direct hybridization of the head and tail ends interferes with the 5' hydrolysis characteristics of probe, and it does not prevent the polymerization of primers and probes (Deming Kong et al., 2003, Acta Chimica Sinica, 755-759). In view of the fact that the sensitivity of fluorescent probe PCR for single molecule detection is obviously insufficient, the current increasing sensitivity method is limited, so additional pretreatment steps are required; at the same time, it is subject to the interference and inhibition of primer-primer and primer-probe non-specific polymerization, even the extremely complex multiple polymerization non-specificity of internal standard system and multiple fluorescent probe PCR. In order to control or eliminate these uncertain multiple polymerization complexities, the present invention "A directionally polymerized fluorescent probe PCR" uses target sequence specific primers and probes design, and at the same time adds artificially directed primers with 5' end reverse complementary sequences; the 3' lengthened end of the fluorescent probe and the middle of the probe is self-complementary reversely pairwise; in addition to specific and strong hybridization with the target sequence, make primers and probes slightly directed to complement each other and combine to eliminate uncertain random hybridization. PCR amplification with complementary 5' ends sequences of the primers brings end complementarity between the amplified products; the 3' ends of the target products can also be templates and primers for each other to increase the amplification efficiency, enhancing sensitivity with >2n series amplification strategy. On the other hand, the 5' ends of the primers are self-complementary and will not extend, which weakens the non-specific polymerization between the 3' ends of the original primer pairs. The 5' end of the fluorescent probe is labeled with fluorescent group the same as the TaqMan probe, only the 3' end is added with a stretch of bases reverse complementary to the middle part and then labeled the quenching group. The probe is similar to a molecular beacon that the 3' end binds to the middle of itself, the quenching group and the fluorescent group complement each other and get closer to inhibit the luminescence, which not only reduces the baseline level but also reduces non-specific polymerization with primers. And A-end primer, probe combined with UDG and mineral oil blocking completely eliminate primer dimer and non-specific amplification of product aerosol.

REFERENCE INFORMATION

[1] Khorana H. G, et al. J. Molec. Biol., 1971, 56(2):341-361.
[2] Sykes P. J.; et al., 1992, BioTechniques, 13:444-449.
[3] Livak K J, et al., 1995, Genome Res: 4:357-362
[4] IV Kutyavin, Nucleic Acids Res., 2010, 38(5)e29.
[5] Tyagi S, et al, 1996, Nat. Biotechnol, 14:303-308
[6] Wittwer, C.; et al., 1997, BioTechniques, 22:130-138.
[7] Brownie J., et al, 1997, Nucleic Acids Res., 25(16): 3235-3241.
[8] Qianfeng Xia. Development and clinical application of dimer mutation primers quantitative PCR technology [D]. 2011, Chongqing Medical University.
[9] Deming Kong et al., 2003, Acta Chimica Sinica, 755-759.

SUMMARY

Polymerase chain reaction PCR exponential amplification or geometric series amplification brings superior detection sensitivity, but the sensitivity is still insufficient for detection of several molecules or even single molecule. The fluorescent probe PCR adds a probe to convert the signal, the specificity is improved, but the sensitivity decrease one order of magnitude And it is subject to the interference and inhibition of non-specific polymerization of primer-primer and primer-probe, even the extremely complex multiple polymerization non-specificity of internal standard system and multiple fluorescent probe PCR. On the other hand, exponential or geometric amplification also brings background primer dimer (PD) and complex non-specific amplification. The small molecule PD/PCR product aerosol contaminate the amplification again. The "closed tube" operation of real-time PCR is not airtight. Even in the case of a closed PCR reaction with mineral oil, the exponential amplification of the trace reaction of the residue of the oil layer is an insurmountable pollution source. Some thinking and concepts in the conventional field of linear detection are not suitable for exponential amplification.

The present invention "A directionally polymerized fluorescent probe PCR", characterized in that on the basis of the specific sequence of primers and probes, set PCR with the 5' end of directed primer pair complementary binding and sensibilization, and 3' tail of fluorescent probe directed polymerization and melting. In primer design, adopting 5-10 bp reverse bases sequence at the 5' end of the original primer pair and adding to the front of the original primer pair in the 5'-3' direction to form a "5' reverse complementary sequence" chimeric primer pair to directionally polymerize, the 3' tails of the amplified products also serve as templates and primers for each other for amplification by dint of 5' end complementation, amplify with >$2^n$ geometric progression to increase sensitivity and competitively reduce primer 3' dimer PD non-specificity, and also reduce the number of amplification reaction cycles. The 3' end of the conventional hydrolysis fluorescent probe is added with a 5-8 bp tail sequence that is reversely complementary to the middle of the probe to form a directed polymerization between any two probe molecules by the tail-middle two parts getting close and hybridizing, the fluorescein and quenching group at both ends of the probe molecule get close, which reduces the baseline fluorescence of the reaction. The distance between the middle complementary region and the 5' end can adjust the amplification baseline level. The probes' self-polymerization also inhibits non-specific polymerization between primers and probes. Once the long-sequence target molecule chain competes for the hybridization primer and probe chain, the pairwise polymerized primer pair and probe with relatively weak binding force melt to bind to the target molecule template for amplification, and the probe is hydrolyzed by polymerase to produce fluorescence.

Said "A directionally polymerized fluorescent probe PCR", characterized in that, use the shorter 5-7 bp of 5' reverse sequence of the opposite original primer as an artificial sequence added to the front of the relative primer, a short 4 bp sequence of restriction site is inserted between the artificially added sequence and the original primer sequence to make the amplified product have the same length after digestion to facilitate electrophoresis detection, meanwhile preset restriction enzyme digestion+UDG digestion measures to prevent cross-contamination of amplified products.

Said "A directionally polymerized fluorescent probe PCR", characterized in that, said primers furtherly has identical sequence of 6-8 bases in the middle to further reduce the level of the primer dimer PD/postpone Ct value of primer dimer background amplification, thereby indirectly reduce PD's competitive inhibition to target amplification and improve system sensitivity.

Said "A directionally polymerized fluorescent probe PCR", characterized in that, said fluorescent probe refers to the 5' end of the template sequence probe is labeled with fluorescein and can be hydrolyzed by the exonuclease activity of DNA polymerase in PCR, add the 5-7b base that is reverse complementary to the middle part of the probe at its 3' end, add an extra base A at the end, and label the quencher group after the tail A; between the added 3' tail and the middle reverse complementary sequence change a base to an "antisense" base, including 2'-Fluoro RNA, 2'-O-Methyl RNA, 2'-O,4'-C-methylene bridge RNA (LNA locked nucleic acid); prevent the non-specific polymerization and extension of the 3' end of the miss-labeled probes, and by pairwise, probes' added 3' tails and the middle reverse complementary sequences hybridized and polymerize directionally; not only strengthen the suppression of baseline fluorescence, but also avoid the non-specific hybridization between the probes and excess primers.

Said "A directionally polymerized fluorescent probe PCR", characterized in that, said primer design is modifying and supplementing some design principles for reducing background, and 5' end directional complementary primer on the basis of conventional primer selection:
  1) Select a pair of primers as the upstream and downstream primer, which has 18-24 bases in length of the sequences and is from both ends of a target-specific (conservative) genes spanning 100-300 bp and has no continuous reverse complementation between the 3' ends of the two primers;
  2) Select a "inverted repeat" with 6-8 bp from the target gene spanning 300 bp, and put it into the middle of the pair of primers and 3-5 bases away from the 3' end, to form middle identical sequence primers pairs;
  3) 5' end reverse complementation—add the 5-8 bp of 5' reverse sequence of the opposite original primer as an artificial sequence to the front of the relative primer, and insert a short 4 bp sequence of restriction enzyme digestion site between the artificially added sequence and the original primer sequence;
  4) Set A/AC as the last bases of the 3' end of the primers pair so that the corresponding dU of amplified product locates in the middle of the junction of the original primer of the dimer; do not choose G ending with many strong hydrogen bond "mismatches", neither T ending with weak hydrogen bond/poor specificity, and don't even use repeated double GG/TT endings.

Said "A directionally polymerized fluorescent probe PCR", characterized in that, said probe design adopts the principles of directionally polymerized fluorescent probe design based on compliance with the general and conventional fluorescent probe design principles:
  1) First select a target fluorescent probe sequence less than 35nt that is close to one side primer has no overlap with the primer, and the Tm value is higher than the primer's Tm value by more than 10° C., and the 5'end of the probe should not be a G base;
  2) The 5'end of the probe is completely the same as the TaqMan hydrolysis probe, which can be labeled with fluorescein FAM, HEX, JOE, VIC, TET, ROX/Texas-Red, or CY5;
  3) Add the 5-7b bases that are reverse complementary to the middle of the probe to its 3' end as the artificially directionally polymerized 3' tail;
  4) An additional A base is added after the 3' end of the probe, and then after the tail A label with the quenching group TAMRA (6-Carboxytetramethylrhodamine), BHQ1 or DABCYL;
  5) From the added 3' end to the middle one base needs to be turned into an antisense "dead" base, which retains the Watson pairing hybridizing performance but loses the functions of amplification template and primer polymerization, and includes 2'-Fluoro RNA, 2'-O-Methyl RNA or 2'-O,4'-C-methylene bridge RNA (LNA locked nucleic acid); the triple setting, the "antisense" base, non-complementary A ending and 3' final quenching group seal, blocks the non-specific polymerization and extension of the 3' end of the miss-labeled probe.

"A directionally polymerized fluorescent probe PCR" according to above, characterized in that, said modified MGB fluorescent probe, the 5' end of the probe that shortens the template hybridization sequence is labeled with fluorescein and is hydrolyzed by Taq enzyme, one base at the 3' end of MGB is changed to an antisense "dead" base, for example: add an extra A tail after 2'-O-M-RNA/2'-F-RNA, tail A is labeled with non-fluorescent quencher NFQ plus a DNA minor groove binding molecule to promote the close binding of the probe and the template, the minor groove binding molecule also hinders non-specific polymerization of its 3'end; the non-fluorescence quenching effect is strong and reduces the background fluorescence background, meanwhile it can better distinguish alleles and can detect single nucleotide polymorphisms (SNP).

Said "A directionally polymerized fluorescent probe PCR", characterized in that, the used concentration of the said primers is 3-5 µM as 40× concentration, and the concentration/dosage of the fluorescent probe correspondingly reduced by half is 2-3 µM as 40×concentration, adjust the best primer and probe concentration according to the minimum concentration detection requirements of different samples and the system background value.

Said "A directionally polymerized fluorescent probe PCR", characterized in that, the PCR reaction solution is added with a universal PCR synergist containing betaine and polyanionic polyphosphoric acid (PPA) to enhance the target amplification efficiency and inhibit the non-specific amplification of primer dimer PD.

Said "A directionally polymerized fluorescent probe PCR", characterized in that, said PCR reaction solution is added with mineral oil instead of using a thermal lid, under the condition of closed PCR reaction solution, adopts one side primer and probe containing 10% sucrose for layering and delaying release, and thermal mixing and starting PCR to reduce the yield of aerosol or produce aerosol of invalid amplification.

Said "A directionally polymerized fluorescent probe PCR", characterized in that, to prevent the target molecule aerosol from causing trace contamination of reagent, prior mixing PCR reagent components/each component firstly add with 0.2%-2% v/v E. coli UDG enzyme, and added with a mixture of 1-2 or more kinds of target sequence restriction endonucleases at a dilute concentration 0.1%-1.0% (v/v) that does not affect target amplification, use the PCR ingredients before mixing being at room temperature for 0.5-2 hours or 37° C. for twenty minutes to forty minutes to digest the cross-contamination of the target template molecules.

Said "A directionally polymerized fluorescent probe PCR", characterized in that, water for PCR and buffer adopt cheap chemical methods instead of enzymatic digestion method to digest pollution, fresh purified water is added with 0.1‰-0.2‰ (v/v) sodium hypochlorite solution, which is one or two in ten thousandths dilution of 10% sodium hypochlorite solution, to digest the contaminated DNA at room temperature for 1-2 days, open the lid and boil to remove sodium hypochlorite; 10×Taq buffer added with 0.05‰-0.1‰ (v/v) exonuclease ExoIII is refrigerated for later use.

Said "A directionally polymerized fluorescent probe PCR", characterized in that, use a closed and independent dosing chamber, sample loading chamber and amplification chamber separated by physical space, mix the PCR reagent ingredients/components in a separate dosing chamber, and perform sample DNA purification and sample loading in a separate sample loading chamber, use the filter tip for sample loading and throw it into the sodium hypochlorite waste solution after use, use pure 1-2% sodium hypochlorite to digest and clean the laboratory regularly before use, and use ultraviolet light and ozone to sterilize before and after the experiment in turn.

Said "A directionally polymerized fluorescent probe PCR", wherein the steps of said fluorescent probe PCR method are as following:
1) Firstly add 2 µL of said slow-release primer+probe containing sucrose to the bottom of each PCR reaction tube;
2) Mix the remaining PCR reagents, and add 18/28 µL of the reaction mixture to the middle of the tube wall of the PCR reaction tube;
3) Add 40 µL of mineral oil along the upper part of the PCR reaction tube wall, centrifuge instantly, and place it at 37° C. for up to 20-40 minutes;
4) Add 20/10 µL of DNA solution extracted from the sample, quantitative standard sample, negative control or positive control under the mineral oil surface, use filter tip, and change tip for each tube;
5) Avoid mixing to avoid damaging the slow-release layer, close the cap of the PCR reaction tube tightly, and centrifuge at high speed instantaneously, perform PCR reaction immediately/as soon as possible, thermal denaturation to mix the slow-release layer and start PCR, and amplify for 36-40 thermal cycles.

Combine said "A directionally polymerized fluorescent probe PCR", characterized in that, said PCR is used for gene detection kit, the kit components include: nucleic acid extraction reagents, 5 mM dNTPs and dUTP, Taq DNA polymerase and its 10× buffer, fluorescent probes, upstream primer F/downstream primer R, standard reference substance, universal PCR synergist, purified water dH2O, mineral oil; or add internal standard primer pair, internal standard fluorescent probe. Reagent ingredients/components are pre-added with 0.2%-2% v/v E. coli UDG enzyme, and added with a mixture of 1-2 or more kinds of target sequence restriction endonucleases at a dilute concentration 0.1%-1.0% (v/v) that does not affect target amplification, digest the cross-contamination of the nucleic acid molecules when preparing the PCR reaction ingredients and inactivate the preset enzymes by PCR thermal denaturation.

Based on the above ideas, the present invention provides a directionally polymerized fluorescent probe PCR Kit, characterized in that, it contains upstream and downstream primers pair and fluorescence labeled probes for target genes, said upstream and downstream primers are further designed and obtained on the basis of a pair of original upstream and downstream primers with a span of the target-specific (conserved) gene 100-300 bp and a length of 18-24 nucleotide bases based on conventional primer design principles; said further design includes:

there is no continuous reverse complementation at the 3' end, and ends with A/AC, a reverse complementary sequence from the 5' end sequence of the original upstream and downstream primers was added to the 5' end of the original upstream and downstream primers, that is, the 5-10b reverse complementary sequence corresponding to the 5' end sequence of the original upstream primer is added to the front of the 5' end of the original downstream primer in the 5'-3' direction, meanwhile, the 5-10b reverse complementary sequence corresponding to the 5'end sequence of said original downstream primer is added in front of the 5' end of said original upstream primer;

Preferably, said further design includes: insert a restriction site sequence between the reverse complementary sequence and the 5' end of the original upstream and downstream primers.

Preferably, said further design includes: set 6-8b in the middle of the original upstream and downstream primers to the same base sequence at 2-6 bases away from the 3' end of the original upstream and downstream primers, so that the upstream and downstream primers form the middle identical sequence primers pair.

Preferably, said fluorescence labeled probe has the following characteristics:

its target sequence is close to one side of the primer pair, its Tm value is higher than the primer's Tm value by more than 10° C., and its 5' end is not end by G base;

its 5' end is labeled with fluorescein; the 3' end has an artificially directionally polymerizing 3' tail sequence that is reversely complementary to its middle 5-7 bp and is obtained by adding bases or changing bases;

an additional A base is added to the end of the 3' tail sequence, and a quenching group is labeled after the Abase, the quenching group is preferably TAMRA, BHQ1 or DABCYL.

Preferably, at least one antisense "dead" base is included in the said 3' tail sequence, which is selected from 2'-Fluoro RNA, 2'-O-Methyl RNA or 2'-O,4'-C-methylene bridge RNA (LNA Locked nucleic acid). This setting allows the probe to retain the pairing hybridization performance but lose the amplification template and primer polymerization functions.

Preferably, said fluorescein is selected from FAM, HEX, JOE, VIC, TET, ROX/Texas-Red or CY5.

Preferably, wherein one side primer is mixed with sucrose solution and fluorescent probe to form a slow-release primer mixture;

the remaining PCR reagents exist in a premixed PCR reaction solution; said PCR reaction solution contains the other side primer, dNTP, Taq enzyme and its buffer, PCR synergist, $dH_2O$; said PCR synergist is betaine and/or polyanionic polyphosphoric acid;

Preferably, the concentration ratio of the fluorescent probe and the primer in the slow-release primer mixture is 1:2.

Preferably, use dU instead of dT in the dNTP of said PCR reaction solution.

Preferably, said PCR reaction solution is also pre-added with 0.2%-2% v/v E. coli UDG enzyme, and restriction endonuclease 0.1%-1% v/v.

Preferably, said kit also contains nucleic acid extraction reagent, standard reference substance, purified water $dH_2O$, and mineral oil; or additional internal standard primer pair, and internal standard fluorescent probe.

A directionally polymerized fluorescent probe PCR provided by the present invention, characterized in that, use the reagents in any of the aforementioned kits to perform PCR on the target gene.

Preferably, take the following steps:
(1) At the bottom of the reaction tube, firstly add a slow-release primer mixture containing one side primer, said fluorescent probe and sucrose;
(2) Add said PCR reaction solution containing the remaining PCR reagents except the template to the middle of the tube wall of the reaction tube;
(3) Add mineral oil to the upper part of the tube wall of the reaction tube, centrifuge instantly, preferably, put the tube at room temperature or 37 degrees Celsius for 20-40 minutes;
(4) Finally, the template is added below the said mineral oil surface, do not mix and immediately centrifuge at high speed for a short time, and then perform PCR reaction.

Real-time fluorescent PCR quantitative analysis is to detect the amount of amplified product (the product indicates the fluorescence intensity) at the time point of the fixed cycle during PCR and directly correlate with the amount of the initial target gene. The Ct value (Cycle threshold) at which the fluorescence signal of the increased amount of amplified product reaches the logarithmic phase, has a negative linear relationship with the logarithm of the initial copy number of the target template. That is, the amplification cycle required for the initial template double dilution to reach the same logarithmic phase fluorescence intensity will increase one cycle (Ct). The real-time fluorescent amplification curve is a dynamic parameter curve which takes the fluorescence intensity generated by the real-time detection of the product binding probe as the ordinate, the number of amplification thermal cycles as the abscissa, and shows the real-time fluorescence intensity as the reaction cycle proceeds. Due to the instability of fluorescence in the first 1-3 cycles of fluorescent probe amplification and the sensibilization by 5 cycles ahead, so the PCR instrument sets the fluorescence value curve of the initial 3-10 cycles of amplification as the background baseline, and defines 10 times the standard deviation of the baseline fluorescence intensity as the threshold value, and the cycle number when the fluorescence intensity reaches the threshold value as the Ct value. Use a series of standard product multiple dilutions of known concentration gradient to calibrate the DNA quantification of the sample to be tested, and take the initial copy log value as the ordinate and the Ct value as the abscissa to make an absolute quantitative calibration curve.

The hydrolysis probe TaqMan is a real-time fluorescent PCR detection oligonucleotide probe. It is designed to be an oligonucleotide (total length <40 nt) which pairs with the sequence between the upstream primer and the downstream primer of the target sequence and try to be as close as possible to one side primer, but does not overlap (more than one base apart). Its 5' end is labeled with a reporter fluorescent group, and the quencher TAMRA (6-Carboxytetramethylrhodamine) is attached to the 3' end. When the probe is complete, through the Forster resonance energy transfer (FRET) effect, it is inhibited as the fluorescence emitted by the fluorescent group close to the quencher, and this results in a fluorescence quenching effect. During the PCR reaction, the complete probe is first paired and hybridized with the target sequence. When the primer anneals and extends, and the newly synthesized DNA strand gets close to the probe hybridization position, DNA polymerase uses its exonuclease activity to cleave the probe to release the reporter fluorescent group into the reaction buffer. When the fluorescent group separates from the quenching group, it emits fluorescence, and DNA strand synthesis continues until the end of the amplification cycles. As the number of amplification cycles increases, the released fluorescent groups continue to accumulate, and the fluorescence intensity is proportional to the amount of amplified products.

Molecular Beacon is a double-labeled oligonucleotide (25-40 nt), forming a pan-like structure with a loop (probe) and a panhandle-like stem (additional sequence) that is complementary to its own end. The fluorescent reporter is labeled at the 5' end, and quenching group with small inhibition range Dabcyl (4-(4-dimethylaminophenylazo) benzoic acid) is labeled at the 3' end. At room temperature, the molecular beacon forms a panhandle-like structure, and the fluorescent reporter and the quenching group are close together through the stem structure formed by the beacon's self-complementation, thus suppressing the fluorescent signal. When PCR denatures and anneals, the molecular beacon encounters the target DNA strand. According to the principle of thermodynamics, the beacon probe will bind to the target DNA instead of forming a panhandle-like structure. Due to the destruction of the panhandle/stem structure, the fluorescent reporter group is relatively separated from the weakly acting quenching group, and the reporter group emits fluorescence correspondingly.

The present invention "A directionally polymerized fluorescent probe PCR" not only inherits the advantages of PCR's exponential amplification and high sensitivity, but the specific sequence of fluorescent probes also bypasses the main non-specificity of primer-dimer amplification and increases reliability of precise hybridization. In addition to using external standard concentration gradient amplification curve for absolute quantification, you can also use target housekeeping gene synchronously/simultaneously as an internal standard to indirectly quantify target molecules. This promotes the use of labeled probes with different wavelengths of fluorescence for multiplex fluorescent PCR; and single-base point mutation probe for single nucleotide SNP polymorphism analysis or subtyping determination. The signal of existing fluorescent probe PCR amplification product has some loss as one more step of probe converting-hydrolyzing fluorophore signal, and each molecular amplification product produces only one hydrolyzed fluorescent group at most, and the fluorescent signal of the probe method is significantly weaker than that of the dye method fluorescent PCR by tens to hundreds of times, so finally the sensitivity of the probe method is one time progression lower than that of the dye method fluorescent PCR. For some single-molecule/single-digit molecules detection and digital absolute quantification of multiple dilution methods, currently the sensitivity of fluorescent probe PCR is obviously insufficient. On the other hand, fluorescent probe PCR has an excess of long-chain probes, internal standard primers, probes, multiple primers and probes, so uncertain primer-primer and primer-probe polymerization non-specific interference and inhibition caused by these excessive amounts of oligonucleotide DNA and even many chaos such as complex polymerization non-specificity of internal standard system and multiple fluorescent probe PCR system, etc. cause it is difficult to control the quality of fluorescent probe PCR.

The present invention "A directionally polymerized fluorescent probe", use directed "5' end complementary" primers to enhance sensitization to reduce non-specificity. A pair of "5' end complementary sequence" primer design uses one side (such as downstream) primer 5' original/self 5-10b reverse complementary sequence as an "artificial sequence" added to the front of the opposite side (upstream)primer 5' end by 5'→3' direction. Conversely, a reverse "artificial sequence" at the 5' end of the opposite primer is added to the front of the one side primer 5' end to produce a pair of chimeric primers. That is, the 5-10b reverse "artificial sequence" added at the 5' end of the primer is reversely complementary to the original 5' end of the opposite primer itself. In this way, the newly generated "5' end complementary sequence" includes the added 5' reverse "artificial sequence" of the original opposite primer+the 5' self-sequence of the original primer; the primer and the "5' end complementary sequence" share an original 5' sequence of the primer, half of the new 5' of the chimeric primers, which is the "5' end complementary sequence", is naturally reverse complementary pairwise, so the 5' end reverse complementary primer can be set to be about 30base long. (The addition of artificial sequences to the 5' end of the primers generally does not affect PCR amplification), using a pair of "5' end complementary sequence" chimeric primers for PCR, the 3' ends of a pair of newly generated replicated strands are complementary to each other correspondingly. The 3' end of the amplified product is not only the template for binding the primer in the subsequent cycle, but also the artificial sequences at the 3' end of the amplified products can be templates for each other, primers for each other to bind, and have exponential amplification. Compared with simple exponential amplification of a pair of primers, it increases the mutual amplification between products, or the gradually increasing 3' end complementary products make up for the primer consumption in the PCR process, and amplification efficiency exceeds >$2^n$ exponential or geometric progression, which achieves enhancing PCR amplification sensitivity; it also increases the fluorescence intensity of amplified products like Snake technology. On the other hand, the "5' end complementary sequence" of the primer is slightly shorter than the primer-target binding sequence which does not affect specific amplification, the directed self 5' end reverse complementation will not cause extension but inhibit the non-specific polymerization between the 3' ends of the original primers, and it eliminates uncertain primer-primer and primer-probe messy polymerization.

When the artificial sequence is shorter, such as 5-7b, a short 4b sequence of restriction site can be inserted between the artificially added sequence and the original primer sequence to make the amplified products have same length after digestion to facilitate electrophoresis identification. In this way, preset restriction digestion+UDG digestion measures can also prevent cross-contamination of amplified products. Fluorescent PCR non-specificity not only comes from the generation of endogenous PD, but also the interference and mutual influence of the aerosol recontamination of exogenous PD product. The lack/de-dU product generated from turacil-DNA glycosylase UDG enzymatically digests ordinary primer dimer PD is still the primer binding template, while it is easier for the "fragments" with complementary bases from non-A-end primer dimer digesting PD to polymerize and become invalid; therefore, using the 3' A ending of the primer corresponding to the junction where dU located in the dimer primer, the de-dU part of middle of the PD product lacks bases for pairing and no template to replicate, which makes the exogenous aerosol PD lose its template function.

Design fluorescent probes based on TaqMan, combining hydrolysis fluorescent probe TaqMan and drawing lessons from the molecular beacon's self-hybridization principle and moving the hybridization region to the middle, and the TaqMan fluorescent probe technology: the probe melt when the amplified product hybridizes. Add a 5-7b artificial tailing base that is reverse complementary to the middle of the probe at the 3' end of the probe, add an additional adenine A base at the end for ending, and then label the quenching group after adenine A. During the sequence from said artificially added tail base to the 3' end A, one base must be changed to an antisense "dead" base, which can be selected from 2'-Fluoro RNA, 2'-O-Methyl RNA or 2'-O,4'-C-methylene bridge RNA (LNA locked nucleic acid), so that it retains Watson pairing hybridizing performance and loses the amplification template and primer polymerization functions. The triple setting of the "antisense" base, non-complementary A ending, and 3' final quenching group block the non-specific polymerization and extension of the 3' end of the miss-labeled probe. The probe added tail and the preset complementary region in the middle of itself or the preset complementary regions of two probes directionally polymerize and hybridize, and the distance between the middle hybridization region and the 5' end determines the level of the amplification baseline. In the present invention, the 5' end of the fluorescent probe is labeled with a fluorescent group like the TaqMan probe, and use Taq enzyme 5'-3' exonuclease activity to hydrolyze the probe hybridizing with the target sequence to cut and release the fluorescent group. Since only the 3' end is added with 5-7b sequence which is reverse complementary to its middle part and then labeled with a quenching group, on one hand, the added end tail of the probe's 3' is similar to molecular beacon turning-back which partially hybridizes with the preset complementary region in the middle of itself intramolecularly. On the other hand, the short hybridization makes it difficult to form a panhandle-like structure. The 3'end of one probe is reversely complementary to the middle of the other free probe, conversely the middle part of the probe also hybridizes with 3' added tail of the other free probe to form a more stable intermolecular pairwise hybridization. The binding force of the two sections of the two probes is large and it is easier to bind stably, which not only makes the quenching group and the fluorescent group complementary and getting close together to strengthen the suppression of the background fluorescence, also avoids forming polymers of non-specific hybridization and extension between the probes and excessive primers, and is compatible with the advantages of molecular beacon baseline/background fluorescence being low and TaqMan not being interfered at close range by quenching groups as hydrolysis releasing fluorescent groups.

The following graphically describes the competitive relationship between primers and probes specific-binding templates and their directed polymerization. Schematic diagram 1 shows the mechanism of increasing sensitivity and reducing non-specificity through exponential amplification of primers combining with templates, and the 3' tails of the products also serving as templates and primers for each other for amplification by dint of 5' end complementation.

Using long lines represents the target template DNA double strands, short arrows represent the upstream and downstream original primers, and arrows indicate the 3' end and the direction of extension and synthesis; the oblique 5' end base letters represent the artificially added "5' end complementary sequence" that does not hybridize to the target template (the letters here only indicate the "5' complementary" state of the primer, and does not specifically refer to the bases currently expressed). The "5' complementary sequence" adopts the 5-10b reverse bases sequence at the 5' end of the opposite original primer, and it is added to the front of the original primer in the 5'-3' direction to form a "5' reverse complementary sequence" chimeric primer. The 3' end target binding segment of the chimeric primer hybridizes and extends, and the replicated strand is indicated by a dashed line. Not only the 5' ends (letter end) between the two molecular products are reverse complementary, but the 3' ends of the new synthetic replicated strands (dotted end) are also reverse complementary, play the role of templates and primers for each other in thermal cycle amplification, and the products can be amplified exponentially by themselves without other free primers.

FIG. 2 shows a TaqMan hydrolysis probe capable of directed self-polymerizing of molecules pairwise, along with the specific template and amplification product compete for binding it will melt and hydrolyze to produce fluorescence. The original probe being added a small tail sequence complementary to the middle of itself makes two probes hybridize pairwise between each other to make the tail quenching group closer to the 5' end fluorescent group, which not only enhances the quenching effect and reduces the baseline fluorescence intensity, but also reduces the non-specific polymerization between the probe and the primer. The thick long line with circles-black dots on two ends represents the probe, the hollow ring indicates the 5' end fluorescent group, and the solid black dot represents the 3' tail quenching group; the main sequence of the probe includes the 5' end base which is completely complementary to the target template sequence, the bent line at the 3' end of the probe represents the artificial tailing sequence that does not hybridize to the target template; by the added 5-7b tail and the reverse complementary sequence of middle of the probe, two probe molecules complementary hybridization and directed polymerization in which one probe's tail hybridized with the middle of the other probe, meanwhile its middle part being hybridized with the tail of the other probe. Once the long-chain target molecules compete for hybridizing with probe strands, the weaker pairwise polymerized probes melt and bind to the said long-chain target molecules, then are hydrolyzed by the polymerase to produce corresponding fluorescence.

Existing real-time fluorescent probe PCR uses probes to bypass the main primer dimer amplification, but the respective directed polymerization of the primers and probes of the present invention further weakens the non-specific polymerization of primer dimer and primer-probe. Because any small amount of non-specific products, even standard product plasmid, free molecules in purified sample DNA will cause aerosol cross-contamination. This can be ignored in conventional linear amplification detection, and once the molecules enter PCR amplification $10^{9-12}$ exponential amplification, the above mentioned pollution will get out of control, and this leads to the macroscopic world concept and conventional linear amplification detection inertial thinking, which hinders the elimination of pollution at the molecular level. Fluorescent PCR non-specificity not only caused by the polymerization PD at the 3' ends of a pair of endogenous primers, but also by the interference and mutual influence produced by repeated pollution of the exogenous PD product aerosol. If the source of endogenous PD non-specificity is not eliminated, it will be difficult to eliminate the product aerosol. On the contrary, if the exogenous aerosol cannot be controlled then it is impossible to study the endogenous PD non-specificity. Because the lack/de-dU product generated from uracil-DNA glycosylase UDG enzymatically digesting ordinary primer dimer PD is still the primer binding template, or because it is easier to polymerize and become invalid for the "fragments" with complementary bases from non-A-end primer dimer digesting PD, and enzymatic hydrolysis is not 100% effective yet when the product aerosol is extremely excessive; therefore, the present invention uses the 3' A end of the primer to make corresponded dU located on the middle part of the junction of original primer in the dimer; the end A of UDG enzymatic digestion primer corresponding to the de-dU part of the middle of the PD product, which is lack of bases to match/bind and has no template to replicate to extend the primer, so UDG enzyme is effective for the dimer product of the primers ending with A/a. Under the condition of PCR combining with mineral oil seal, adopts a component such as one primer comprising 10% sucrose for layering to delay and slow the starting of release—thermal mixing to reduce the output of aerosol, or lead to invalid amplification by making the aerosol lack of completed components. Such a simple step is indeed the most effective and necessary means to completely solve the cross-contamination of exponential amplification at the molecular level. The mineral oil layer will not affect the fluorescence light path or fluorescence intensity.

In addition to the main pollution source of small molecule PD, the laboratory aerosol pollution also includes the purified free molecules of target DNA, especially the quantitative standard product plasmid is also the source of molecular level pollution. It cannot be removed by filtration with ordinary filter membrane, and it is easy to cross-contaminate the PCR reagents; and it is also easy for the purified water to dissolve the aerosol molecules; and pollution lasts long during freezing storage in the refrigerator. To prevent cross-contamination of such aerosol, PCR reagents must be produced in a sterile and nucleic acid free environment, and the reagent ingredients/components prepared with fresh purified water should be pre-added with 0.2%-2% v/v E. coli UDG enzyme. (Add a mixture of 1-2 or more kinds of restriction endonucleases of the target sequence at a dilute concentration 0.1%-1% v/v, which does not affect target amplification), using the restriction endonucleases to digest cross-contamination of nucleic acid molecules when subpack the PCR reagents. A large amount of PCR water can also be added 0.1‰ about 1/10,000 volume of sodium hypochlorite stock solution (10%) for long time digestion, and remove sodium hypochlorite by autoclaving disinfection/boiling. Prepare 10×Taq buffer and add 0.05‰-0.1‰ volume of exonuclease ExoIII. During application testing, separate spaces for dosing, sample loading, and amplification must be separated. The prepared PCR liquid mixture can be put in room temperature for 30-60 minutes before sample loading, using preset enzyme to digest molecular contamination. Run PCR heat denaturation after loading the sample to inactivate the pre-added preset restriction endonucleases.

Sealing with mineral in of the early PCR was gradually replaced by the thermal lid of the instrument. However, the thermal lid of fluorescent PCR was not completely sealed in the case of "closed tube analysis". Most 0.2 ml PCR test tubes or 96-well plates, when denatured at 95° C. under thermal cycling, some aerosol will overflow (be squeezed out) along the edge of the thermally softened tube cap under high temperature and high pressure. An aerosol particle contains $10^6$ molecular copies. The aerosol not only contains a high concentration of amplified positive target molecules, but contains small molecule primer dimer PD amplification produced between excessive pairs of primers. Almost every detection reaction tube/well will produce PD non-specific exponential amplification, and the re-contamination of the small molecule PD amplification product aerosol cannot be avoided only by filtration and GMP. As the same PCR is repeated, the leaked contaminants will be exponentially amplified and accumulated repeatedly, and the subsequent real-time fluorescent PCR does not start from cycle 0 but from the cycles number at the end of the last PCR, the pollutants accumulate more and more by repeated PCR amplification. The product aerosol not only pollutes the laboratory environment, but also enters all open reagents including water for experiment, and stored for a long time with the refrigeration reagents. The PD product contamination of a pair of primers is also non-specifically amplified at 30 Ct/cycle, which is gradually advanced by repeated PCR. When mineral oil is used in combination with a thermal lid, during the reaction process, the residual reaction liquid on the surface of the mineral oil will not be evaporated to the thermal lid but will continue to remain on the surface of the mineral oil; as the reaction conditions change, it will also go through the cycle processes, producing more aerosol containing amplified products. When the thermal lid is not used, the residual liquid on the surface of the mineral oil will evaporate to the tube cover, which is far from the reaction solution under the mineral oil, and it's easy for it to anneal at the lower temperature but is not easy for thermal denaturation, so no amplification of it, and the aerosol produced is also less. Therefore, in real-time fluorescent quantitative PCR detection, the PCR reaction solution is added with mineral oil instead of using a thermal lid. Under the condition of closed PCR reaction solution, adopt one side primer and probe containing 10% sucrose for layering and delaying release, and thermal mixing and starting PCR to reduce the yield of aerosol or produce invalid amplified aerosol. However, it is necessary to use mineral oil plus thermal lid if the PCR instrument is with the emission light source located over the PCR tube cover, because the condensate of the residual liquid on the surface of the mineral oil evaporated to the tube cap will block the light path to a certain extent.

Principles of Primer Design of the Present Invention "a Directionally Polymerized Fluorescent Probe PCR":

Based on the current primer selection principle, (1) Generally, select the target-specific (conservative) sequence with 18-24 nucleotide bases in length, the length difference of the upstream and downstream primers should not be greater than 3 bases, and the difference between the two Tm values should not be greater than 5° C., and the suitable span of the upstream and downstream primers on the target gene is 100-300 bp. (2) G+C content should be 40%-60%, 4 kinds of bases distribution/match should be uniform. Avoid secondary structures of identical repeat of more than 4 bases, sequence reverse repeats (hairpin structure), and sequence simple repeats. (3) Between a pair of primers there should not be a continuous reverse complementation of 3 bases or more than 3 bases, especially the reverse complementation of the 3' ends. (4) The 3' end bases of the primer, especially the last and penultimate bases, should be correctly paired with the target. Try to make the 3' last base of each primer to be G/C, but neither be NNCG or NNGC end (the so-called CG/GC clip), nor the T end with poor specificity.

There are still some cognitive differences in the existing primer selection principles, which need to be modified and added with some new rules to reduce background and directionally complement: 1) Middle identical sequence—select 6-8b "inverted repeat" from the target gene of 100-300 bp span, put it into the middle of a pair of primers, 3-5 bases away from the 3' end of the primers. 2) 5' end reverse complementation—add the 5-8b of 5' reverse sequence of the opposite original primer as an artificial sequence to the front of the relative primer, and insert a short 4b sequence of restriction enzyme digestion site between the artificially added sequence and the original primer sequence. 3) Select A as the 1st or 2nd base of the 3' ends of a pair of primers for ending to make the corresponding dU of product locates in the middle of the junction of the the original primer of the dimer; the uracil-DNA glycosylase UDG digesting the end A of primer, make the de-dU part of the middle of PD product be lack of bases of replication template and cannot perform PD amplification. 4) It is best to choose A/AC ending for the 3' last base of each primer, should not choose G ending, which has strong hydrogen bond and "mismatches", neither T ending, which has weak hydrogen bond/poor specificity, and don't even use repeated double GG/TT endings.

TaqMan Probe Design Follows the Following General Principles:

Based on the existing probe selection principles: (1) The Tm value of the probe is more than 10° C. higher than the Tm value of the primer. (2) The 5' end of the probe should not be a G base, the G that is digested and degraded by restriction enzyme still has the function of quenching the reporter fluorescence. (3) The G in the probe should not be more than C. (4) Avoid stringing of single nucleotide, especially G (5) When the probe is annealed, its 5' end should be as close to the primer as possible without overlapping, and at least one base away from the 3' end of the primer. (6) The 3' end of the probe must be blocked with a quencher to prevent extension during PCR amplification.

Some new principles for the directionally polymerized probes must also be added: 1) Add the 5-7b bases that are reverse complementary to the middle of the probe to its 3' end. 2) Add an Abase for ending at the probe 3' end, and then label the quenching group after the tail A. 3) One base needs to be turned into an antisense "dead" base in the added 3' tail sequence, which retains the Watson pairing hybridizing performance but loses the functions of amplification template and primer polymerization, and includes 2'-Fluoro RNA, 2'-O-Methyl RNA or 2'-O,4'-C-methylene bridge RNA (LNA locked nucleic acid); the triple setting of the "antisense" base, extra non-complementary A ending, and 3' final quenching group blocks to prevent the non-specific polymerization and extension of the 3' end of the miss-labeled probe.

The present invention "A directionally polymerized fluorescent probe PCR", firstly it is necessary to establish effective test methods and tools, and test out various directionally polymerized primers and the experimental conditions and scope of fluorescent probes PCR. Fluorescent hydrolysis probe PCR itself is a good tool for testing the conditions and scope of fluorescent probe PCR and directionally polymerized fluorescent probe PCR. Use the test purpose or target PCR components change and different test conditions to establish the conditions and boundary range of fluorescent PCR.

The PCR reaction solution is prepared with PCR components from Sangon Biotech (Shanghai) Co., Ltd, such as dNTPs, Taq DNA polymerase, synthesized fluorescent probes, upstream primers/downstream primers. Use the SLAN-96P real-time fluorescent PCR instrument of Shanghai Hongshi company to perform two-step thermal cycle fluorescent probe PCR reaction of 35-40 thermal cycles of 94° C. denaturation for 20 seconds, 58-62° C. annealing, and extension for 40 seconds, and analyze the experimental results.

The following formula is the standard procedure of preparation method of reaction solution for directionally polymerized fluorescent probe PCR. The single reaction is the concentration of each component of PCR and the amount of preparations, and the slow-release primer solution contains 10% sucrose by weight. The formula 10×times reaction is convenient for the calculation and preparation of a set of test reaction solutions, and the corresponding 25 times or 50 times the volume of PCR components of a single reaction is a kit component.

| Probe PCR components | single reaction | 10 × times reaction |
|---|---|---|
| slow-release primer(2 μM) and probe(1 μM) | 2.0 μl | |
| opposite primer(4 μM) | 1.0 μl | 10 μl |
| dNTP(10 μM dU replaces dT) | 0.6 μl | 6 μl |
| Taq(2.5 U/μl) | 2.0 μl | 20 μl |
| 10 × Taq buffer | 4.0 μl | 40 μl |
| PCR synergist(20×) | 2.0 μl | 20 μl |
| dH2O purified water | 8.5(/18.5) μl | 85(/185) μl |
| template/test object | 20(/10) μl | |
| total volume | 40 μl | 200(/300) μl |

※10×Taq buffer: 0.6M Tris-Cl (pH8.3), 100 mM KCl, 50 mM $(NH_4)_2SO_4$.

Slow-release primer+probe=1.0 unit volume of 4 μM primer+(0.5 unit volume of 4 μM probe+0.5 unit volume of 20% sucrose) and mix well.

In this probe method fluorescence PCR, add 20/10 μl volume of a series of standard DNA gradient dilutions and purified DNA solution of the target molecule sample to be tested separately to a set of standard 40 μl reaction system for fluorescence PCR. It is also ok to add water instead of the amplification template to test the primer dimer PD background and the impact on background amplification of the PCR system without target template.

Add components in the following order:
(1) Add 2 μL of the slow-release primer+probe to the bottom of each PCR reaction tube (no need to change the tip).
(2) Add 18/28 μL of the remaining reaction mixture to the middle of the tube wall of the PCR reaction tube (be careful and no need to change the tip).
(3) Then carefully add 40 μL of mineral oil along the upper part of the PCR reaction tube wall, centrifuge instantly, and place it at RT/37° C. for up to 60 minutes.
(4) Finally add 20/10 μL of DNA solution of extracted from the sample/quantitative standard product/negative control/positive control under the mineral oil surface (use filter tip, change tip for each tube, put the tip into the 5% sodium hypochlorite waste solution tank after use, and seal the tank).
(5) Do Not mix, avoid damaging the slow-release layer, close the PCR reaction tube cap tightly, and centrifuge at high speed instantaneously. Perform PCR reaction immediately/as soon as possible, thermal denaturation would mix the slow-release layer and start PCR, and amplify for 36 thermal cycles.

Instrument standard PCR program settings: first denature at 94° C. for 3-5 minutes, run 35-40 thermal cycles for denaturation at 94° C. for 20 seconds, annealing at 58-62° C., extension for 40 seconds and read the fluorescence value; or 35-40 cycles of denaturation at 94° C. for 20 seconds, annealing at 54° C. for 10 seconds, extension at 60° C. for 35 seconds, and read the fluorescence value for oil-sealed PCR without thermal lid amplification. For special test purposes, such as testing to optimize the primer PCR background, the number of thermal cycles can be increased. The baseline of the instrument is set at the initial 3-10 cycles to avoid the detection window that moves forward 5 cycles after sensibilization, take 10 times the standard deviation of the baseline fluorescence value as the threshold, and the cycle number at which the fluorescence reaches the threshold is the Ct value. Samples with a Ct value of less than 30 cycles are considered positive, and greater than 32 cycles are considered negative; samples with a Ct value between 30-32 gray zone should be retested.

Below, using primers and probes sequences of example 1 to pre-test the experimental conditions and scope of the directionally polymerized probe PCR:

The conventional HBV primers are as follows:

HBvF:
(SEQ ID NO. 1)
5'-aat gcc cct <u>atc tta tca</u> ac-3'

HBvRa:
(SEQ ID NO. 2)
5'-aga ttg aga <u>tct tat</u> gcg ac-3'

The sequence of the directed 5' complementary primer pair is as follows:

5'THBVF:
(SEQ ID NO. 3)
5'-tca atc tcc gga aat gcc cct <u>atc tta tca</u>-3'

5'THBVRa:
(SEQ ID NO. 4)
5'-ggc att tcc gga gat tga <u>gat ctt atg</u> cga c-3'

(The bold letters represent the restriction enzyme hpaII site, the thin letters represent the HBV sequence, and the underlined parts are the identical sequence)

The sequences of conventional probes and directed 3' complementary probes are as follows:

TaqManHBv:
(SEQ ID NO. 5)
5'-FAM-cgt ctg cga ggc gag gga gtt ctt ctt cta a-BHQ₁-3'

Melting TqMnHb:
(SEQ ID NO. 6)
5'-FAM-cgt ctg cga ggc *gag gga g*tt ctt ctt <u>ctc cc</u>/i2ome<u>T</u>/<u>c</u>a-TAMRA-3'

(The bold black italic letters and the underlined parts represent the reverse complementarity between the two probes, and/i2ome T/is the antisense "dead" base)

Quickly prepare ×N times of single PCR reaction mixture according to the following table. The ×N represents a single PCR reaction times by the number of PCR reaction tubes or the total number of detections. Test 10 reactions this time:

downstream primer R+probe as slow-release primer-probe, which is mixed with 1.0×volume of 4 μM primer+(0.5× volume of 4 μM probe+0.5×volume of 20% sucrose). Add 2 μL of slow-release primer-probe, 28 μL of PCR reaction solution, 40 μL of mineral oil to each tube in turn, and finally add 10 μL of stand sample I-VII DNA under the oil layer. Perform fluorescent PCR immediately after transient high-speed centrifugation. Run oil-sealed PCR amplification without thermal-lid of denaturation at 94° C. for 3 minutes firstly, running 36 cycles of denaturation at 94° C. for 20 seconds, annealing at 54° C. for 10 seconds and extension at 60° C. for 35 seconds, and read the fluorescence value.

| | reaction reagent | | | | | |
|---|---|---|---|---|---|---|
| | one primer | dNTP | Taq enzymes | 10 × Taq buffer | PCR synergist | dH2O | total volume |
| dosing volume μL | 1.0 × N | 0.6 × N | 2 × N | 4.0 × N | 2 × N | 8.5/18.5 · N | 18(28) × N |

Test the sensibilization effect of the maximum and minimum values of the detection window/range boundary of the fluorescent probe PCR with 5' directionally polymerized primers, and use primers 5'THBVF/5'THBVRa fluorescent TaqManHBv probe PCR to determine pHBc (3.36 kb, molecular weight MW=2.1×10$^6$, 1 μg=2.8×10$^{11}$ copy molecules) plasmid standard product 10× dilution gradient, standard I (10 ng/mL), II, III, IV, V and standard VI (0.1 g/mL×10$^{-6}$). Compare with conventional primers HBvF/HBvRa fluorescent TaqManHBv probe PCR detecting standard I and standard VI.

Because the 5' reverse complementary primers make up for the primer consumption due to the gradually increasing ends of the amplified product as amplifying, the amount of primers required for 5' directionally complementary primer fluorescent PCR is slightly less than conventional PCR, only 3-5 μM (as 40×, final concentration 0.1 μM) primers are sufficient to amplify single molecule for detection. The primers of this test used primers of concentration 4 μM (as 40×) according to the above recipe table, and loading standard products were standard I-VI plasmids 10 μL, and performed real-time fluorescent PCR of 39 thermal cycles.

The results are shown in FIG. 3 and Table 3 below: the Ct value corresponding to the standard products of 5' directed complementary polymerization primer standard product I—standard product VI respectively is 11.0, 14.4, 17.7, 21.0, 24.0, 27.1; compared with the Ct value of conventional primers with standard product I 16.4, and standard product VI 32.5, the Ct value was about 5 cycles earlier respectively, that is the 5' directed complementary primer PCR has nearly 5.5 cycles of sensibilization increase compared with conventional primers, Ct value≈50 times magnification. Every 10 times dilution there is still about 3.3 cycles interval, the standard gradient interval is basically unchanged, and it does not affect the standard curve gradient.

TABLE 3

| | Standard gradient | | | | | |
|---|---|---|---|---|---|---|
| | Stand I | Stand II | Stand III | Stand IV | Stand V | Stand VI |
| Directed primer Ct | 11.0 | 14.4 | 17.7 | 21.0 | 24.0 | 27.1 |
| Conventional primer Ct | 16.4 | | | | | 32.5 |

DETAILED DESCRIPTION OF THE EMBODIMENTS

Figure 1:
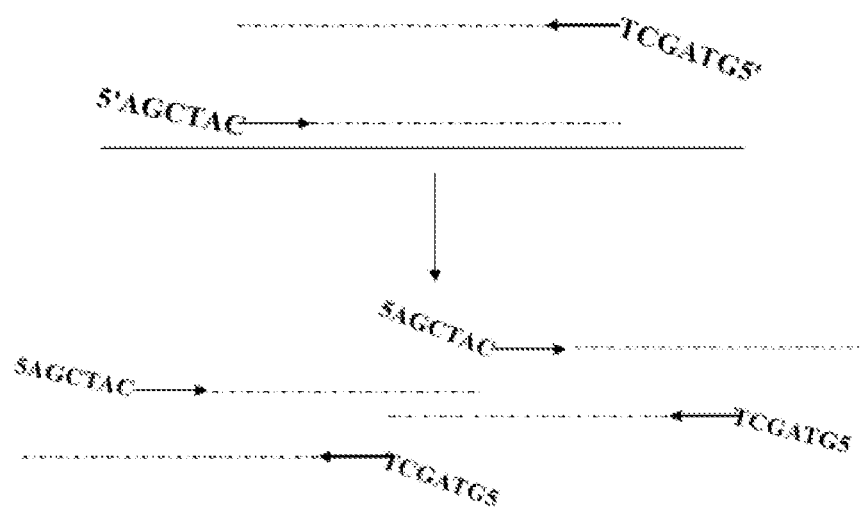
FIG. 1 is the schematic diagram of the directed polymerization of 5' complementary primers, with long lines representing the target template DNA double strands, short arrows representing the upstream and downstream original primers, and arrows indicating the 3' end and the direction of extension and synthesis; the oblique 5' end base letters represent the artificially added "5' end complementary sequence" that does not hybridize to the target template, indicating that the chimeric primer 5' reverse complementation which makes the 3' end (dotted line end) of the two molecule products are also reverse complementary, being template and primer to each other for amplification.
Figure 2:
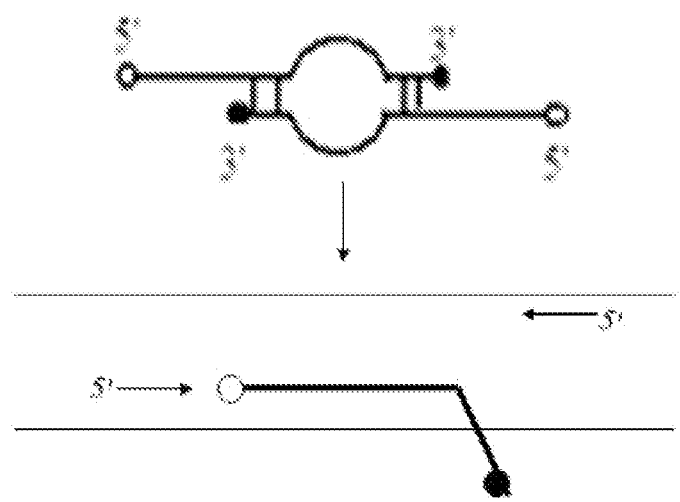
FIG. 2 is the schematic diagram of 3' directed polymerization of melting type hydrolysis probe, the long line represents the template sequence, the thick long line with circles-black dots on two ends represents the probe, the hollow ring indicates the 5' head end fluorescent group, and the solid black dot represents the 3' tail quenching group; the main sequence of the probe includes the 5' end bases which are completely complementary to the target template sequence, the bent line at the 3' end of the probe represents the tail sequence that does not hybridize to the target template. The added 5-7b tails and the reverse complementary sequences of middle of any two probe molecules form a TaqMan hydrolysis probes, in which there is two close positions by one probe's tail being complementary to the middle part of the other probe, and at the same time its middle part hybridizing with the other probe's tail. The TaqMan hydrolysis probes can directedly self-polymerize, and will produce fluorescence along with the competitive binding of the specific amplification products and being melt and hydrolyzed
Figure 3:
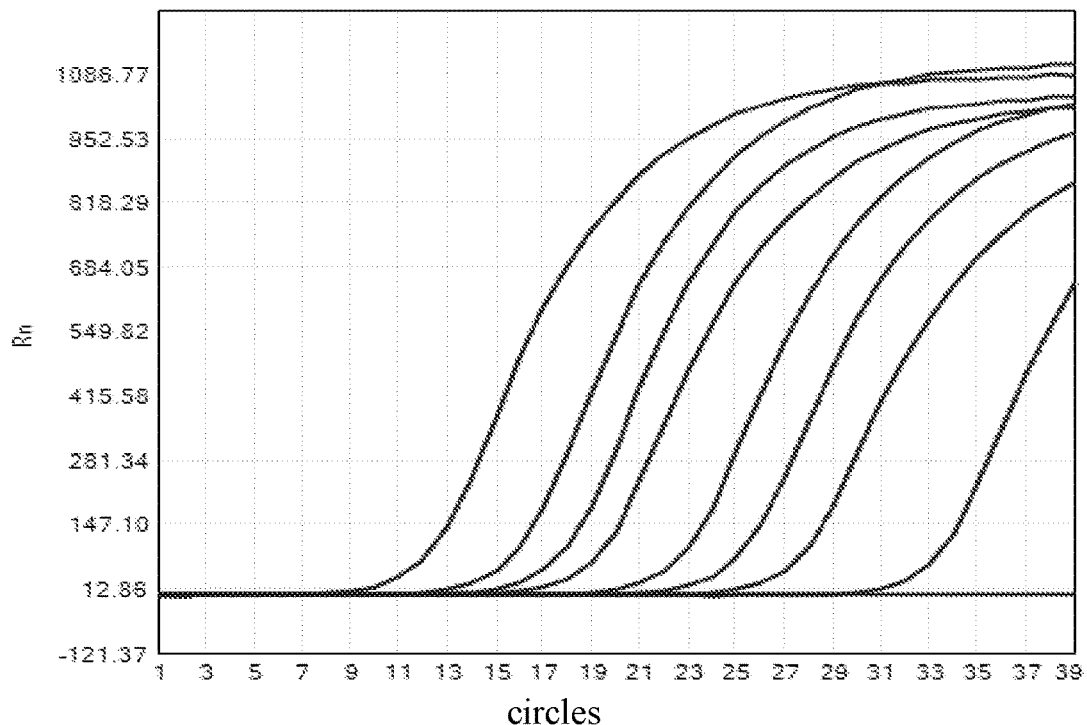
FIG. 3 is amplification curve of standard products fluorescent probe PCR with primer of 5' directed polymerization, the amplification Ct value of corresponding standard products standard product I—standard product VI respectively is 11.0, 14.4, 17.7, 21.0, 24.0, 27.1; compared with the Ct value of conventional primers with standard product I 16.4, and standard product VI 32.5, the Ct value was about 5 cycles earlier respectively, the maximum value and minimum value of the detection range boundary are both sensitized by nearly 5.5 cycles Ct value≈nearly 50 times magnification; every 10 times dilution there is still about 3.3 cycles interval, the standard gradient interval is basically unchanged.

The following examples further illustrate the content of the present invention, but should not be understood as a limitation to the present invention. Without departing from the spirit and essence of the present invention, any modification or substitution made to the method, conditions, steps, and applications of the present invention belong to the scope of the present invention.

Example 1: Human Hepatitis B Virus Directionally Polymerized Fluorescent Probe PCR Viral hepatitis type B (hepatitis B for short) is a worldwide Class III infectious disease infected by Hepatitis B virus (HBV). According to the World Health Organization WHO, about 2 billion people worldwide carry HBV. The rate of hepatitis B infection among the population in our country is very high (nearly 10%). Liver cancer, which is mainly caused by hepatitis virus, ranks first among tumors, which greatly endangers the health of the people. At present, the detection methods of hepatitis B mainly include enzyme immunoassay 5 items/7 items, chemiluminescence method, immunofluorescence method, nucleic acid amplification (PCR) fluorescence quantitative method, etc. Traditional enzyme immunoassay is widely used, but the sensitivity is insufficient. Real-time fluorescent PCR quantification and digital quantitative PCR methods can accurately determine the viral load of hepatitis of patients, and have an irreplaceable important role in learning the level of virus replication in infected patients, and monitoring the infectiousness of the disease and the efficacy of antiviral drugs. Most of the target regions for nucleic acid amplification are chosen from a conserved sequence in the S region of Hepatitis B virus (HBV) and a conserved sequence in the C region of HBV, but the secondary structure block of the S region and the primer background is high. We chose a sequence of HBV C region (nt:1901-2497) and cloned into pUC19 vector plasmid pHBc (MW 2.1×10$^6$) as the positive template sequence for hepatitis B virus. A selected sequence of hepatitis B virus (HBV) Core region (CDR: 2306-2444) is used as a nucleic acid amplification target specific sequence for HBV conventional primers and 5' end reverse complementary primers, and the Core region (nt: 2306-2444) sequence of about 20 bases at both ends is shown as follows:

```
AB540584 Core region (nt: 2306-2444)
CAAATGCCCC TATCTTATCA AC   - GTCGCAGAAGA TCTCAATCTC
(SEQ ID NO. 7)               (SEQ ID NO. 8)
```

According to the comprehensive consideration based on the general primer selection principles to minimize primer dimers and Chinese patent (A method of reducing dimer with a pair of partially identical primers, China, CN201010105371.8) partially identical primers: selected a segment of reverse identical/"primer identical sequence" bases from the conserved region of HBV C and placed it in the middle of the primer pair. Since 5 bases of the identical sequence in the middle were not enough, in the situation of not affecting the target amplification efficiency, one base was mutated to increase the number of "identical sequence" bases. The 7b identical sequence in the middle could selectively reduce the primer dimer PD non-specificity with more than 10 Ct values. The conventional HBV primers for fluorescent probe PCR were as follows:

```
HBvF:
                                     (SEQ ID NO. 1)
     5'-aat gcc cct atc tta tca ac-3'

HBvRa:
                                     (SEQ ID NO. 2)
     5'-aga ttg agatct tat gcg ac-3'
```

5' End Reverse Complementary Primer of HBV Core Antigen C Region:

Added the reverse sequence ggcattt of the 5' end of the upstream primer to the front of the 5' end of the downstream primer, and spaced with the restriction enzyme hpaII site ecgg; added the reverse sequence tcaatct at the 5' end of the downstream primer to the front of the 5' end of the upstream primer, and spaced with the restriction enzyme hpaII site ecgg; formed a chimeric primer pair and end with a/ac;

The sequence of the directed 5' complementary primer pair was as follows:

```
5'THBVF:
                                          (SEQ ID NO. 3)
5'-tca atc tcc gga aat gcc cct atc tta tca a-3'

5'THBVRa:
                                          (SEQ ID NO. 4)
5'-ggc att tcc gga gat tga gat ctt atg cga c-3'
```

(The bold letters represent the restriction enzyme hpaII site, the thin letters represent the HBV sequence, and the underlined parts are the identical sequence)

Design of Directionally Polymerized Probe for HBV Core Antigen C Region:

For using the melting type TaqMan hydrolysis probe, selected a representative sequence (nt: 2368-2397) of the target gene (near the downstream primer) as the target specific sequence (/complementary sequence), that was the probe sequence, and labeled the 5' end with reporter fluorescent dye FAM. The probe hybridized with the target sequence can be hydrolyzed byTaq enzyme 5'-3' exonuclease activity and to release the fluorescent group. The 3' end of the probe was set with 5-7b bases as an artificially directionally polymerized 3' tail sequence that are reversely complementary to the middle gag gga g of the probe. An additional base A was added to the end of the 3' tail sequence, and the quenching group TAMRA (6-Carboxytetramethylrhodamine) and BHQ1 were labeled after the tail A. In the added 3' tail sequence, set one base as the "antisense" base 2'-O-Methyl RNA. The triple setting i.e. the "antisense" base, non-complementary A ending, and 3' final quenching group was used to block the non-specific polymerization and extension of the 3' end of the miss-labeled probe.

Although the hybridization binding part in the probe is short, which makes it is difficult to form a panhandle structure by itself, but the two segments between the two probes have a strong binding force so it's easy to complement each other and bind together. This not only enhances the suppression of background fluorescence, but also avoids the formation of polymers of non-specific hybridization and extension between the probe and excess primers. With both the advantages of low molecular beacon background and strong free fluorescence of TaqMan, it can eliminates or obviously reduce the exponential amplification of primer and probe polymerizing which interferes detection results.

The sequences of conventional probes and directed 3' polymerization probes are as follows:

TaqManHBv: 5'-FAM-cgt ctg cga ggc gag gga gtt ctt ctt cta a-BHQ$_1$-3' (SEQ ID NO.5)

melting TqMnHb: 5'-FAM-cgt ctg cga ggc gag gga gtt ctt ctt ctc cc/i2omeT/ca-TAMRA-3' (SEQ ID NO.6)

(The bold black italic letters and the underlined part represent the reverse complementarity between the two probes, and/i2ome T/is the antisense base)

Because the viral load of hepatitis B virus is much higher than other diseases infection source, and the sensitivity of PCR with 5' directed complementary primers is 50 times higher than that of conventional PCR, the 5' directed complementary primer PCR of hepatitis B virus HBV can be used for ultra-sensitive detection.

(1)DNA Extraction from Clinical Blood Samples:

The blood samples contain excessive PCR inhibitors such as hemoglobin, heme, and immunoglobulin IgQ so DNA must be purified.

Column centrifugation method: took 200 μL of plasma, added an equal volume of saturated phenol/chloroform/isoamyl alcohol (25:24:1) to extract once, then used chloroform to extract once. Added 3 times of DNA binding buffer (6M sodium iodide NaI) to the supernatant then transferred to a commercial DNA purification column (Plasmid Minipreparation purification column, detailed steps were carried out according to Qiagen/Tiagen instructions). Washed the column twice with wash buffer (2M NaI containing 70% EtOH), added 40 μL dH2O to elute and collected the purified sample. A large volume of phenol-chloroform extract must be precipitated with 1/10 volume of 3M sodium acetate (pH 5.2) and 2.5 times absolute ethanol or an equal volume of isopropanol.

PEG precipitation method: Took 100 μL of serum, added 100 μL of 16% PEG salt solution, vortex mixed, centrifuged at high speed for 10 minutes. Discarded the supernatant, added 50 μL of boiling lysis buffer to the remaining concentrated precipitate, mixed gently, boiled for 10 minutes in boiling water or a metal bath, centrifuged at high speed for 10 minutes, and the supernatant was the extracted DNA solution.

2×boiling lysis buffer: 0.02N NaOH, 0.02% SDS (w/v), 25 mM KoAc, 10 mM $(NH_4)_2SO_4$, 0.5% G25(v/v), 0.5M Betaine, 0.5% Glycerol (v/v) 和 0.05% Gelatin (w/v).

Micro magnetic beads method: used guanidine hydrochloride/guanidine isothiocyanate to lyse, nucleic acid was bound to the hydroxyl group of silanized surface of polystyrene micro-magnetic beads under the condition of high concentration of 4M guanidine salt. Washed with buffer less than pH 6.0, eluted with buffer greater than pH 8.5. (The micro magnetic beads method has increasingly replaced the phenol-chloroform extraction method and the silicon adsorption membrane centrifugal column method.)

Took 100 μL of serum into a 1.5 mL EP tube, added an equal volume of guanidine salt lysis buffer for 5 minutes, added 0.8 mL diluted neutralization solution, then added 25 μL of paramagnetic nano silicified spheres to bind. Placed the test tubes in a magnetic separation test tube rack to adsorb and fix the micro magnetic beads. After discarding the solution, added 0.8 mL wash buffer to wash once, and finally added 50 μL of elution solution to the micro magnetic beads to collect DNA.

(3) Standard Gradient and Sample Detection of TaqMan Fluorescence PCR Reaction:

Since TaqMan probe PCR releases at most one fluorescent group per template per cycle, the fluorescence intensity of the reaction is much lower than the SYBR Green I fluorescent dye method (Each 3-4 bp DNA can bind one SYBR Green I molecule), so the TaqMan method must use a larger-volume of 40 μL reaction system so that the PCR instrument can receive a fluorescent signal with sufficient intensity.

Quickly prepared ×N times of single PCR reaction mixture according to the following table. ×N represented a single reaction times by the number of PCR reaction tubes or the total number of detections. Tested 10 reactions this time: downstream primer R+probe as slow-release primer-probe, which was mixed with 1.0×volume of 4 μM primer+ (0.5×volume of 4 μM probe+0.5×volume of 20% sucrose). Added 2 μL of slow-release primer-probe, 28 μL of PCR reaction solution, 40 μL of mineral oil to each tube in turn, and finally added 10 μL of DNA of stand sample I-VII under the oil layer. Performed fluorescence PCR immediately after transient high-speed centrifugation. Thermal starting of slow-release primer effectively prevented product aerosol pollution.

| | reaction reagent | | | | | | |
|---|---|---|---|---|---|---|---|
| | one side primer | dNTP | Taq enzymes | 10 × Taq buffer | PCR synergist | dH2O | total volume |
| dosing volume μL | 1.0 × N | 0.6 × N | 2 × N | 4.0 × N | 2 × N | 8.5/18.5 × N | 18(28) × N |

A total of 0.56 mL of the reaction mixture prepared was divided into PCR reaction tubes or 8-strip tubes pre-added with slow-release primers, 28 μL per tube, divided into 20 tubes. Slowly added 40 μL of mineral oil along the tube wall to seal, carefully added 10 μL of DNA to be tested under the oil layer in sequence. Added 10 μL of purified water dH2O to one of the tubes as the negative control of the PCR system, centrifuged for a short time, remember not to mix! Prevent damage to the release layer. For the reliability of the test results, positive and negative controls and quantitative calibrators (according to whether quantitative requirements are required) must be established for each test.

Put the reaction tubes into real-time fluorescent PCR machine (adjust the excitation light wavelength FAM: 480 nm, detection light wavelength FAM: 520 nm). Set the operating program according to the instruction manual, first performed denaturation at 94° C. for 3 minutes, then ran 36-39 cycles of denaturation at 94° C. for 20 seconds, annealing at 58-60° C., extended for 40 seconds and read the fluorescence value. This is an oil-sealed PCR amplification without thermal lid.

Each test could be parallelized with 2×40 μL to calculate the average Ct value, and analyzed the statistical results.
Quantitative Gradient Standard Curve:

Used hepatitis B virus HBV core antigen C gene cloning plasmid pHBc (0.1 μg/ml) as a template as a 10×(fold) dilution series gradient standard product I(0.1 μg/ml× $10^{-1}$), ×$10^{-2}$×$10^{-1}$, ×$10^{-4}$×$10^{-5}$×$10^{-6}$, ×$10^{-7}$. Calculated with pUC-HBcore (3.36 kb, molecular weight MW=2.1× 106, 1 μg=2.8×1011 copy molecules), the corresponding standard products' gradient molecule copy number was, standard product I: 2.8×$10^9$ copies/mL, II: 2.8×$10^8$ copies/mL, III: 2.8×$10^7$ copies/mL, IV: 2.8×$10^6$ copies/mL, V: 2.8×$10^5$ copies/mL, VI: 2.8×$10^4$ copies/mL and standard product VII: 2.8×$10^3$ copies/mL.

Figure 4:
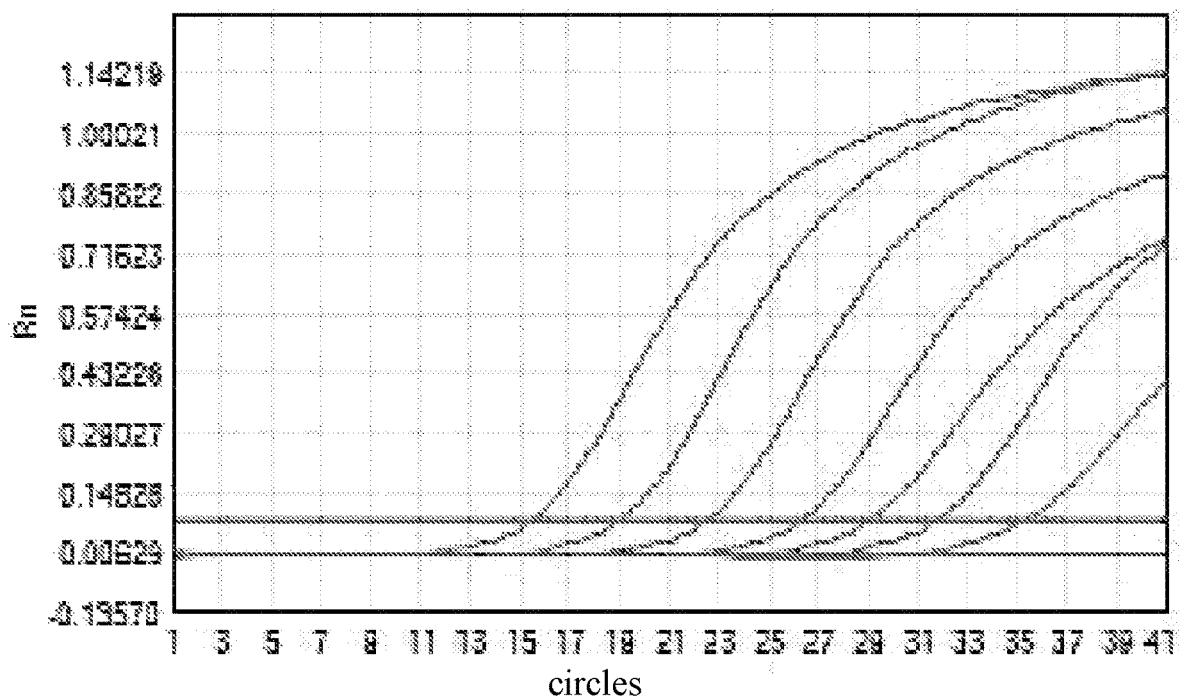
FIG. 4 is the curve of hepatitis B virus conventional primer hydrolysis probe real-time fluorescent PCR detection with standard product pHBcore by 10-fold dilution, results show the Ct values of standard product I (10 ng/mL)—standard product VII detected are 15.6, 19.1, 23.2, 26.4, 29.3, 31.5, 35.4 respectively, the Ct value of the background control is basically a straight line within 40 cycles.
Figure 5:
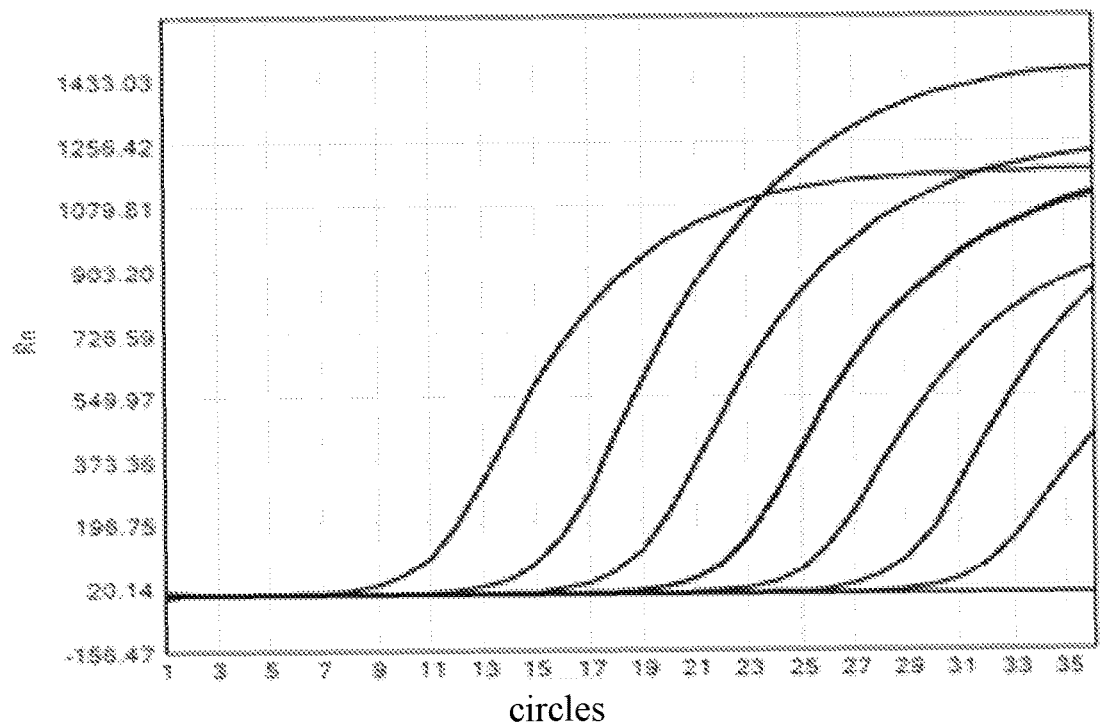
FIG. 5 is results of HBV directionally polymerized primer fluorescent probe PCR: the gradient amplification curves corresponding to the concentration gradient of the 7 standard products by 10-fold dilutions, the primer 5'HBVcF/5'HBVcRa gradient standards product I-standard product VII corresponds to the Ct value of 10.0, 13.8, 17.4, 21.0, 24.3, 27.7, 31.2 cycles.
Figure 6:
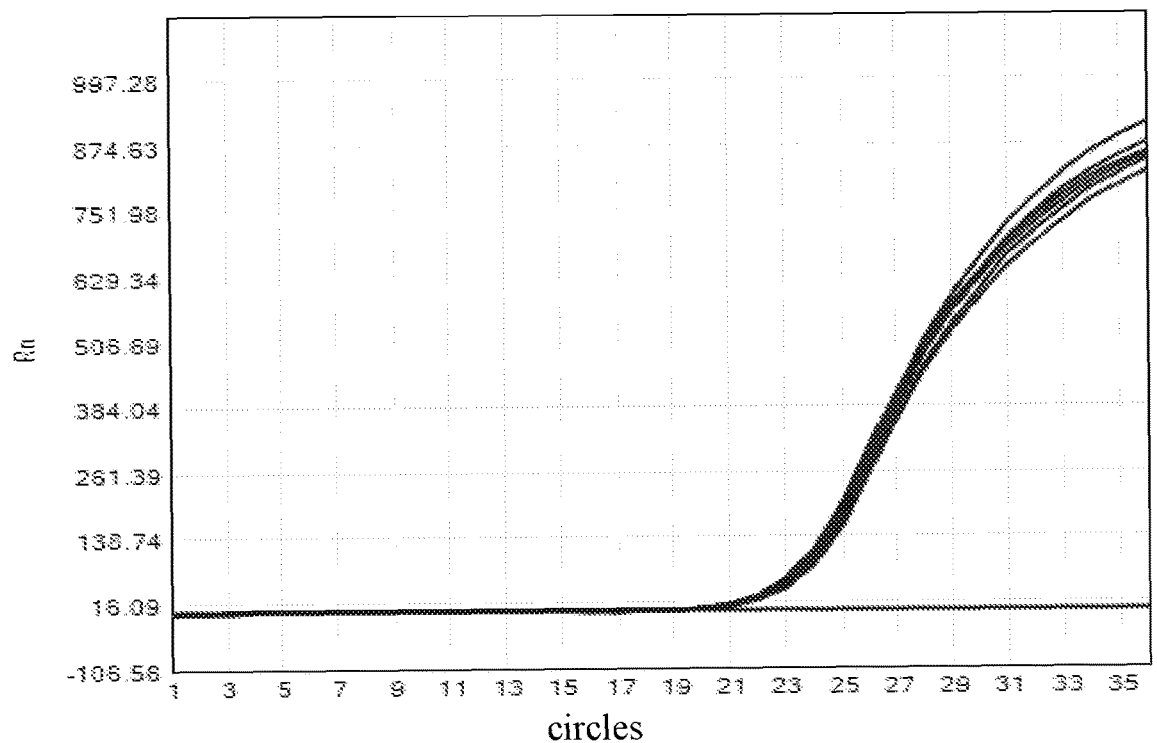
FIG. 6 shows by adding β-globinas internal standard exon2, the average Ct value of directionally polymerized primer fluorescent probe PCR is 23.5 cycles.

Analysis of experimental results: the gradient amplification curve corresponding to the 10-fold dilution concentration gradient of the 7 standard products was shown in FIG. 5. The corresponded Ct values of Primer 5'HBVcF/5'HBV-cRa gradient standard product I-VII were 10.0, 13.8, 17.4, 21.0, 24.3, 27.7, 31.2; internal standard's Ct value was 23.5, shown as in FIG. 6. The first amplification curve on the far left of the standard quantitative curve of HBV core antigen plasmid control pUC-HBcore was corresponding to 2.8×$10^9$ copies/mL, followed by a 10-fold dilution, and the gradient interval of the amplification curve was uniform and repeatable. The last amplification curve was a background control without template. As a result, the Ct value of the background control was basically a straight line within 36 cycles, and there was no amplification Ct value in the PCR reaction. For comparison with the standard product I-VII amplification curve of the conventional fluorescent probe PCR, as shown in FIG. 4, the 5' directed complementary primer amplification was nearly 5 Ct values ahead.

The hepatitis B virus (HBV) nucleic acid quantitative standard product: (batch number 0711) linear sensitivity reference products was purchased fromNational Institutes for Food and Drug Control (NIFDC) and used to test the directionally polymerized fluorescent probe PCR: the linear sensitivity reference products was set as L0-L6,3 repeats. Result showed the linear sensitivity reference products L0-L5 were all positive, and the quantitative concentration value also met the given reference range, and the correlation coefficient $R^2$ was not less than 0.98. Tested positive reference products P1-P9, and the test results were all positive. The negative reference products were all baseline reaction. The sensitivity of the linear sensitivity reference products could reach Ct35-37.

(3) Internal Standard-Globin—Globin Design and Experiment:

Because some residual PCR inhibitor components during DNA extraction interfere with the detection of PCR samples and suppress PCR sample detection, false negative reactions are generated. Therefore, probe method PCR with internal standard amplification of different fluorescence wavelengths occurred, and the false negatives caused by the PCR inhibitor components are monitored through internal standard gene amplification. In recent years, PCR with internal standard amplification probes using different target sequences such as housekeeping genes has become a regular standard procedure. Adding an internal standard with a known starting copy number to the sample to be tested, the PCR reaction becomes a duplex PCR. There is interference and competition between the two templates in the duplex PCR reaction. When the internal standard and the target template competitively share the same primer, it will cause significant interference when the initial copy number difference is greater than 10 times. For non-competitive internal standard amplification with different primers, with a concentration difference of more than 100 times, the amplification of the two templates gradually interferes and inhibits.

Hepatitis B virus HBV directionally polymerized fluorescent probe PCR hypersensitivity detection kit, used housekeeping gene human-globin as the internal standard gene, mutated and cloned into the plasmid pUC-globin2 as the internal standard template. Scheme 1 adopted the method of adding internal standard to clinical specimens: comprehensively consider the non-specific polymerization and amplification between the internal standard amplification primers and the HBV fluorescent probe PCR primers, interfering and inhibiting HBV directionally polymerized fluorescent probe PCR, we chose-globin exon2 as the template and primer sequence, artificially inserted the atcttat of the identical sequence in the middle of the HBV primer into the middle of the exon2 internal standard primer pair, mutated template and internal standard primers with most unchanged but middle identical sequence:

Tβg2F:
(SEQ ID NO. 9)
5'-atg ggc *atc tta t*aa ggt gaa-3'

Tβg2R:
(SEQ ID NO. 10)
5'-ga gg*a tct tat* agg tga gcc a-3'

(Bold black and italic letters represent the identical sequence in the middle of the HBV primer, the rest is the exon2 sequence, the underlined part is the identical sequence)
The 5' reverse complementary primer pair of internal standard inserted into the middle identical sequence:

5'TβgF:
(SEQ ID NO. 11)
5'-g atc ctc cgg atg ggc atc tta taa ggt gaa-3'

5'TβgR:
(SEQ ID NO. 12)
5'-gc cca tcc gga gga tct tat agg tga gcc a-3'

(The bold letters represent the restriction enzyme hpaII site, the thin letters represent the internal standard primer sequence, and the underlined part is the identical sequence)
The sequence of the human-globin internal standard probe TaqMan g is as follows:

(SEQ ID NO. 13)
5'-HEX-ctc atg gca aga aag tgc tcg gtg cct
t/i2omeT/aa-BHQ1-3'

(4) Clinical Trial Results:

Clinically studied 700 clinical samples compared to the kit of Shanghai clone biological High Tech Co., Ltd., the clinical samples including 332 cases of chronic hepatitis B, 156 cases of acute hepatitis B, 56 cases of hepatitis B carriers, and 6 cases of liver cancer, therein 103 cases of B genotype, 436 cases of C genotype, 11 cases of D genotype; 8 cases of liver cirrhosis, 7 cases of liver cysts, 8 cases of hepatitis C, 3 cases of hepatitis A, 2 cases of hepatitis E, 102 cases of healthy people, 20 cases of diabetes and other diseases. Including 10 interference samples (4 hemolysis samples, 3 lipemia samples, and 3 triglyceride samples), the test results were all negative, indicating that the interfering substances had no significant effect on the test results.

The results shows that the Ct values were all 3-5 cycles ahead than the reagents of Shanghai clone biological High Tech Co., Ltd. The positive quantitative coincidence rate was 99.64%, the negative coincidence rate was 98.01%, and the overall coincidence rate was 99.29%. After Kappa test, the kappa value was 0.966, which was greater than 0.8, indicating that the test results of the two reagents were highly consistent.

The measured value of this reagent was the Y variable, and the measured value of the contrast reagent was the X variable. Fitted the linear regression equation, Y=0.969×+0.373, the slope (95% confidence interval) was 0.969, P<0.001, and the linear regression equation was statistically significant (F value 46518.951, P<0.001), the correlation coefficient (R) was 0.993, P<0.001, $R^2$ was 0.985. It showed that the test results of the two reagents were highly correlated.

Example 2: *Mycobacterium tuberculosis*-Directionally Polymerized Fluorescent Probe PCR Tuberculosis is a chronic wasting infectious disease caused by *Mycobacterium tuberculosis*. It can invade many organs, but mainly the lungs, and it is called tuberculosis. Respiratory tract transmission from person to person is the main way of transmission of this disease, and the source of infection is contact with TB patients who excrete bacteria. With factors such as AIDS, drug abuse, immunosuppressant application, population migration and other factors, the incidence of tuberculosis is increasing. According to the WHO report, one out of every three people in the world has been infected with *Mycobacterium tuberculosis*. Every year, 8 million new cases occur and 3 million die from the disease, ranking the first cause of disease death in my country.

At present, the detection mainly uses sputum tuberculosis microscopic examination/tuberculous *bacillus* culture, tuberculin OT/PPD test, enzyme immunoassay ELISA, and X-ray filming, etc. However, the culture period of *Mycobacterium tuberculosis* is long and the positive detection rate is not high. Therefore, the detection of *Mycobacterium tuberculosis* by polymerase chain reaction (PCR) technology can greatly improve the detection rate and specificity of detection. Mostly the repetitive sequences of the *Mycobacterium tuberculosis* genome are selected, and the inserted sequences have 1-20 copies of IS6110 and IS986 which are the first choice of the PCR detection template to further improve the detection rate.

Design of the 5' End Reverse Complementary Primers of *Mycobacterium tuberculosis*:

Added the 5' reverse sequence cgc cta of the upstream primer to the 5' end of the downstream primer and spaced it with ccgg, and added the 5' reverse sequence agc gat of the downstream primer to the 5' end of the upstream primer and spaced it with ccgg to form a chimeric primer pair, and ended with c a.

```
5'TTBF:
                                        (SEQ ID NO. 14)
    5'-agc gat ccg gta ggc gaa ccc tgc cca-3'

5'TTBR:
                                        (SEQ ID NO. 15)
    5'-cgc cta ccg gat cgc tga tcc ggc cac a-3'
```

(Bold letters represent restriction enzyme hpaII sites, thin letters represent TB repeat sequences)

The sequence of the directed 3' polymerization probe is as follows:

```
Melting TBTqMn:
                                        (SEQ ID NO. 16)
    5'-FAM-cac ata ggt gag gtc tgc tac cca cag ccg
    acc/i2ome T/ca-TAMRA-3'
```

(The bold black italic letters and the underlined parts represent the reverse complementarity between the two probes, and/i2ome T/is the antisense base)

Extraction of Virus DNA by Precipitation Boiling Method and Standard Procedure for Directional Polymerization of Fluorescent Probe PCR:

(2) DNA Extraction from Sputum Samples:

Simple boiling lysis method, firstly added lysozyme to lyse the sputum, took 100 μl-200 μl and added the same amount of boiling lysis buffer (mixed the micro beads well before use, cut a large mouth pipette to absorb), mixed gently, and placed in a boiling water bath for 10 minutes. After a brief cooling at 4° C., centrifuged at high speed for 10 minutes, and took 10 μl of the supernatant ras loading sample. Or a large amount of lysate supernatant can be further purified by magnetic micro beads adsorption reagent.

2×boiling lysis buffer: 0.02NNaOH, 0.02% SDS (w/v), 25 mMKoAc, 10 mM $(NH_4)_2SO_4$, 0.5% G25(v/v), 0.5M Betaine, 0.5% Glycerol (v/v) 和 0.05% Gelatin (w/v).

(2) Standard Gradient and Sample Detection Sensibilization PCR Reaction:

Quickly prepared ×N single PCR reaction mixture according to the following table. ×N represented a single multiplied by the number of PCR reaction tubes or the total number of detections. Tested 10 reactions this time: downstream primer R+probe as slow-release primer-probe, which was mixed with 1.0×volume of 4 μM primer+(0.5×volume of 4 μM probe+0.5×volume of 20% sucrose). Added 2 μL of slow-release primer-probe, 28 μL of PCR reaction solution, 40 μL of mineral oil to each tube in turn, and finally added 10 μL of DNA of stand sample I-stand sample VII under the oil layer. Performed fluorescence PCR immediately after transient high-speed centrifugation. Hot start of slow-release primer effectively prevented product aerosol pollution.

| reaction reagent | | | | | | |
|---|---|---|---|---|---|---|
| one side primer | dNTP | Taq enzymes | 10 × Taq buffer | PCR synergist | dH2O | total volume |
| dosing volume μL  1.0 × N | 0.6 × N | 2 × N | 4.0 × N | 2 × N | 8.5/18.5 · N | 18(28) × N |

Used Hongshi SLAN-96P fluorescent PCR instrument for real-time fluorescent PCR, firstly denatured at 95° C. for 3 minutes, then ran 36 cycles of denaturation at 94° C. for 20 seconds, annealing at 58° C.-60° C., extended for 40 seconds and read fluorescence value. It is oil-sealed PCR without thermal lid amplification.

*Mycobacterium tuberculosis* gene cloning plasmid pUC-TBis (0.1 μg/ml) was used as a template, made a 10×(fold) dilution series gradient standard product I(0.1 μg/ml×$10^{-1}$), ×$10^{-2}$, ×$10^{-3}$, ×$10^{-4}$, ×$10^{-5}$, ×$10^{-6}$, ×$10^{-7}$.

Figure 7:
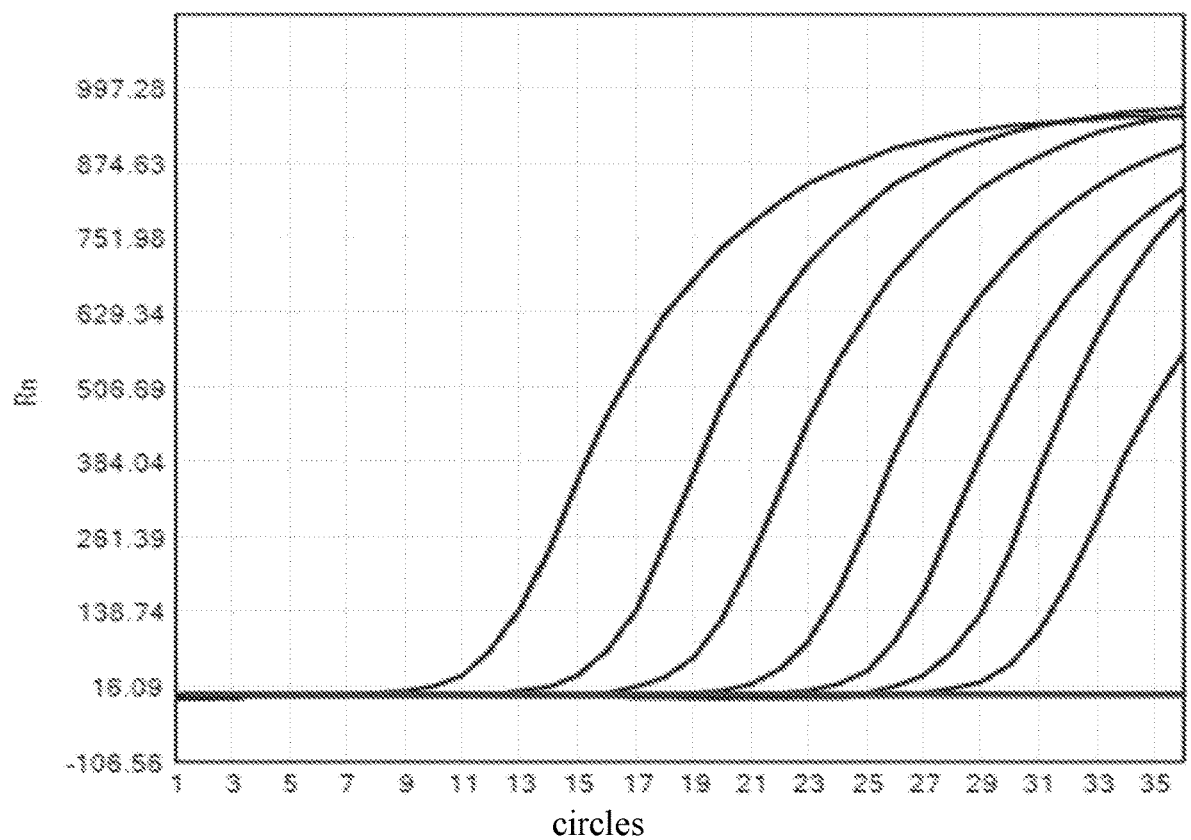
FIG. 7 is the result of Mycobacterium tuberculosis directionally polymerized primer fluorescent probe PCR: the gradient amplification curves corresponding to the concentration gradient of the 7 standard products by 10-fold dilution, the primer 5'TTBF/5'TTBR gradient standard product I-standard product VII correspond to the Ct value 11.5, 15.1, 18.5, 21.8, 25.0, 27.6, 30.0 cycles.

Analysis of the experimental results: the gradient amplification curves corresponding to the 10-fold dilution concentration gradient of the 7 standard products were shown in FIG. 7. The primer 5'TTBF/5'TTBR gradient standard product I-standard product VII corresponded to the Ct value 11.5, 15.1, 18.5, 21.8, 25.0, 27.6, 30.0 cycles.

What is claimed is:

1. A method for detecting a target gene using a polymerized fluorescent probe PCR, comprising the steps of:

designing an upstream primer and a downstream primer for a target gene comprising:

selecting a pair of upstream and downstream sequences, each having 18-24 bases in length, from a target gene having a base span of 100-300 bp, inserting 2-6 bases away from the 3' end of the downstream sequence a first artificial sequence comprising a first reverse complementary sequence of 5-10 bases corresponding to a 5' end sequence of the upstream-sequence and a first restriction enzyme site sequence inserted between the first reverse complementary sequence and the insertion 2-6 bases away from the 3' end of the downstream sequence, to form the downstream primer;

inserting 2-6 bases away from the 3' end of the upstream-sequence a second artificial sequence comprising a second reverse complementary sequence of 5-10 bases corresponding to the 5' end sequence of the downstream-sequence and a second restriction enzyme site sequence inserted between the second reverse complementary sequence and the insertion 2-6 bases away from the 3' end of the upstream sequence, to form the upstream primer;

and detecting the target gene with the first upstream primer and the downstream primer, comprising:

premixing a primer mixture comprising one of either the upstream primer or the downstream primer, sucrose solution, and a fluorescent probe; and premixing a PCR reaction solution, which contains the other of the upstream or the downstream primer which is not added to the primer mixture, dNTP, Taq enzyme and a PCR buffer, dH$_2$O; wherein the dNTP contains dU and does not contain dT;

at a bottom of a reaction tube, adding the primer mixture;

adding the PCR reaction solution to a wall of the reaction tube above the primer mixture;

adding mineral oil to the wall of the reaction tube above the PCR reaction solution, centrifuging, and putting the reaction tube at a temperature of 37° C. for 20-40 minutes; and then adding template below the surface of the mineral oil without mixing, and centrifuging, then performing a PCR reaction whereby the 5' end sequences of the original primer pair in the first artificial sequence and second artificial sequence allows the upstream primer and downstream primer to polymerize, so that 3' tails of amplification products serve as templates and primers for each other for amplification.

2. The method for detecting the target gene according to claim 1, wherein the upstream primer and the downstream primer each further comprise an identical sequence of 6-8 bases.

3. The method for detecting the target gene according to claim 1, wherein the fluorescent probe:
   (1) is labeled with fluorescein at a 5' end of the fluorescent probe, and the fluorescent probe can be hydrolyzed by an exonuclease activity of DNA polymerase in PCR;
   (2) has 5-7 bases 3' tail sequence, at its 3' end, that is reversely complementary to 5-7 bases in part, allowing any two probe molecules to polymerize, and the 3' of a first probe and a second probe will hybridize; and
   (3) an extra A base added at the 3' tail sequence and a quencher group is labeled after the base A; and
   (4) at least one antisense dead base is included in the 3' tail sequence of the fluorescent probe, which is selected from the group consisting of: 2'-Fluoro RNA, 2'-O-Methyl RNA, or 2'-O,4'-C-methylene bridge RNA.

4. The method for detecting the target gene according to claim 1, wherein the fluorescent probe has the following characteristics:
   1) the fluorescent probe has a length of less than 35 nt, and on the sequence of the target gene, the fluorescent probe is close to the upstream original primer or the downstream original primer and has no overlap with either primer, and a Tm value of the fluorescent probe is higher than a Tm value of the upstream primer and downstream primer by more than 10° C., and a 5'end of the fluorescent probe is not a G base;
   2) the 5' end of the fluorescent probe is identical to a common TaqMan hydrolysis probe, wherein the fluorescent probe is labeled with fluorescein FAM, HEX, JOE, VIC, TET, ROX/Texas-Red, or CY5;
   3) the fluorescent probe has 5-7b bases added to its 3' end as an artificially polymerized 3' tail sequence, which is reversely complementary to part of the probe;
   4) the fluorescent probe has an additional non-complementary tail A base after the 3' tail sequence, and the tail A is labeled with a quenching group;
   5) one base located between the 3' tail sequence and part of the probe is an antisense base, wherein the antisense base retains Watson pairing hybridizing performance but loses amplification function and primer polymerization function, and the antisense base comprises 2'-Fluoro RNA, 2'-O-Methyl RNA or 2'-O,4'-C-methylene bridge RNA; wherein the antisense base, non-complementary tail A base ending, and the quenching group blocks extension of the 3' end.

5. The method for detecting the target gene according to claim 1, wherein a tail A of the probe is labeled with a non-fluorescent quencher NFQ and a DNA minor groove binding molecule, wherein the DNA minor groove binding molecule promotes binding of the probe and the template.

6. The method for detecting the target gene according to claim 1, wherein a PCR synergist is added to the reaction tube to inhibit the non-specific amplification of primer dimer PD, wherein the PCR synergist comprises betaine and polyanionic polyphosphoric acid (PPA).

7. The method for detecting the target gene according to claim 1, wherein to prevent contamination of reagents from target molecule aerosol 0.2%-2% v/v E. coli UDG enzyme is first added, and a mixture of 1 or more target sequence restriction endonucleases at a concentration of 0.1%-1.0% (v/v) are added to the PCR reaction solution before the PCR reaction, wherein the mixture of 1 or more target sequence restriction endonucleases do not affect target amplification, and target template molecules are digested at room temperature for 0.5-2 hours or 37° C. for twenty minutes to forty minutes to prevent cross-contamination.

8. The method for detecting the target gene according to claim 1, wherein the dH$_2$O used in the PCR reaction solution has been sterilized by adding 0.1%-0.2% (v/v) of 10% sodium hypochlorite solution to digest contaminated DNA at room temperature for 1-2 days, and then boiling the dH$_2$O with lid open so as to remove the sodium hypochlorite; and 10×Taq buffer with 0.05%-0.1% (v/v) exonuclease ExoIII is added to the PCR reaction solution and PCR reaction solution is then refrigerated for later use.

9. The method for detecting the target gene according to claim 1, wherein the PCR reaction solution is mixed in a dosing chamber, and a sample DNA purification and a sample loading are performed in a sample loading chamber, and wherein the dosing chamber, the sample loading chamber and an amplification chamber are separated by physical space.

10. The method for detecting the target gene according to claim 1, wherein a concentration ratio of the fluorescent probe to either the upstream primer or downstream primer in the primer mixture is 1:2.

* * * * *